United States Patent
Howell et al.

(10) Patent No.: US 6,639,623 B2
(45) Date of Patent: Oct. 28, 2003

(54) CONTROLS FOR A SURGICAL THEATER SYSTEM

(75) Inventors: Charles A. Howell, Batesville, IN (US); Jonathan D. Turner, Dillsboro, IN (US); Howard Reed, Warsaw, IN (US); Richard H. Heimbrook, Cincinnati, OH (US); Scott Manlove, Osgood, IN (US); Gary A. Gray, Union, KY (US)

(73) Assignee: Hill-Rom Services, Inc., Batesville, IN (US)

( * ) Notice: Subject to any disclaimer, the term of this patent is extended or adjusted under 35 U.S.C. 154(b) by 347 days.

(21) Appl. No.: 09/747,605

(22) Filed: Dec. 22, 2000

(65) Prior Publication Data

US 2001/0030683 A1 Oct. 18, 2001

Related U.S. Application Data
(60) Provisional application No. 60/173,027, filed on Dec. 23, 1999, provisional application No. 60/193,892, filed on Mar. 31, 2000, and provisional application No. 60/240,870, filed on Oct. 13, 2000.

(51) Int. Cl.[7] .......................... H04N 7/18; G03B 15/02
(52) U.S. Cl. .................... 348/61; 348/370; 348/373; 362/11
(58) Field of Search .......................... 348/61, 77, 143, 348/370, 373; 362/8, 11, 147, 403–404; 360/160, 172, 175, 178

(56) References Cited

U.S. PATENT DOCUMENTS
3,240,925 A   3/1966   Paschke et al.
(List continued on next page.)

FOREIGN PATENT DOCUMENTS
| DE | 3312137 | 10/1984 |
| DE | 8913757.4 | 3/1991 |
| DE | 29818108 | 3/1999 |
| FR | 2 759 580 | 8/1998 |

*Primary Examiner*—Vu Le
(74) *Attorney, Agent, or Firm*—Barnes & Thornburg

(57) ABSTRACT

A surgical light apparatus includes a hub assembly configured to be attached to a ceiling, and an arm coupled for pivotal movement about the hub assembly. In certain embodiments, a monitor is mounted on a monitor mount attached to the arm. The monitor mount includes a handle on which a first actuator is mounted. A video input controller is electrically coupled to the monitor. The video input controller includes a first channel input having a video coupling for attachment to a first video input device providing a first video feed, a second channel input having a video coupling for attachment to a second video device providing a second video feed, and a channel controller coupled to the monitor, the first channel input, and the second channel input. The channel controller is coupled to the first actuator and is configured to select a video feed to the monitor in response to actuation of the first actuator. In certain embodiments, a camera mount is mounted to the arm. The camera mount includes a handle on which a second actuator is mounted. A camera is mounted on the camera mount. The camera includes an on/off function, automated zoom capabilities, and automated focus capabilities. Actuation of the second actuator controls the on/off function of the camera.

21 Claims, 22 Drawing Sheets

U.S. PATENT DOCUMENTS

| | | | |
|---|---|---|---|
| 3,810,209 A | 5/1974 | Bahnsen | |
| 4,416,293 A | 11/1983 | Anderson et al. | |
| 4,503,854 A | 3/1985 | Jako | |
| 4,598,311 A | 7/1986 | Bellina | |
| 4,625,938 A | 12/1986 | Brown | |
| 4,710,819 A | 12/1987 | Brown | |
| 4,844,252 A | 7/1989 | Barron et al. | |
| 4,963,903 A | 10/1990 | Cane | |
| 5,165,786 A * | 11/1992 | Hubert | 362/287 |
| 5,543,832 A | 8/1996 | Oravecz et al. | |
| 5,713,545 A | 2/1998 | Nakamura | |
| 5,772,593 A | 6/1998 | Hakamata | |
| 5,808,680 A | 9/1998 | Steckhan | |
| 5,867,210 A | 2/1999 | Rod | 348/51 |
| 5,901,200 A | 5/1999 | Krause | |
| 5,961,456 A | 10/1999 | Gildenberg | |
| 6,020,917 A | 2/2000 | Oravecz et al. | |
| 6,023,289 A | 2/2000 | Oravecz et al. | |
| 6,088,612 A | 7/2000 | Blair | |
| 6,096,025 A * | 8/2000 | Borders | 606/1 |
| 6,160,582 A | 12/2000 | Hill | |
| 6,231,527 B1 | 5/2001 | Sol | |
| 6,328,458 B1 * | 12/2001 | Bell et al. | 362/371 |
| 6,402,351 B1 * | 6/2002 | Borders et al. | 362/395 |
| 6,443,596 B1 * | 9/2002 | Bulko et al. | 362/293 |
| 6,464,383 B1 * | 10/2002 | Northington et al. | 362/572 |
| 6,471,363 B1 * | 10/2002 | Howell et al. | 362/11 |
| 2002/0089857 A1 * | 7/2002 | Borders et al. | 362/399 |
| 2002/0172033 A1 * | 11/2002 | Bulko et al. | 362/33 |

\* cited by examiner

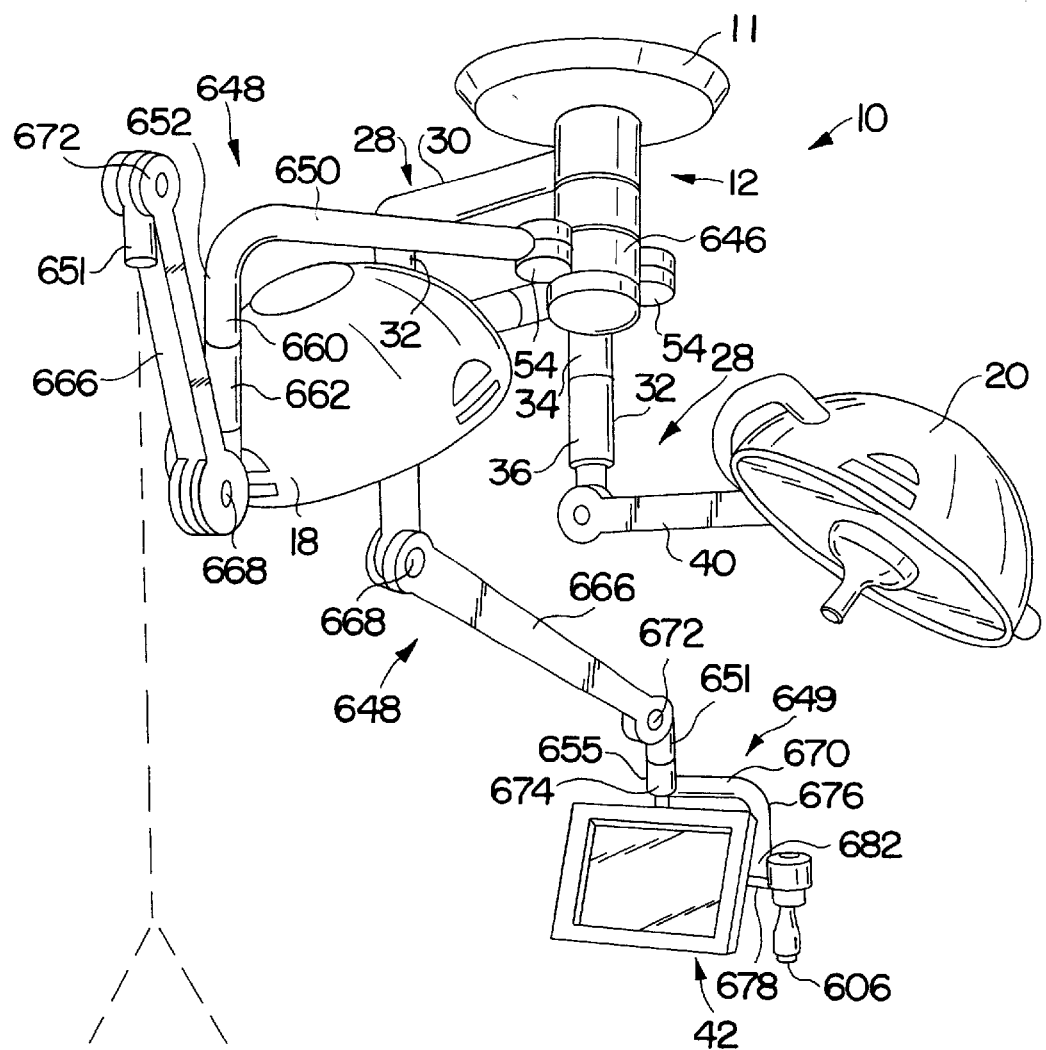
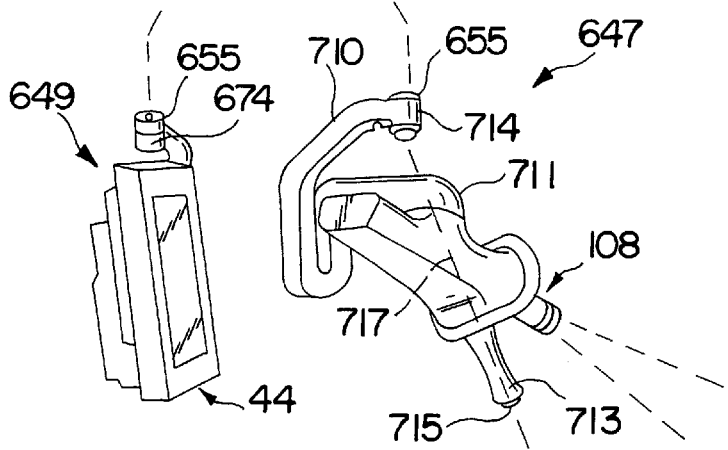
FIG. 16

CONTROLS FOR A SURGICAL THEATER SYSTEM

This application claims benefit Prov. No. 60/173,027 filed Dec. 23,1999 and claims benefit of Prov. No. 60/193, 892 filed Mar. 31, 2000 and claims benefit of Prov. No. 60/240,870 filed Oct. 13, 2000.

BACKGROUND AND SUMMARY OF THE INVENTION

The present invention relates to a ceiling mounted system for use in a surgical theater. More particularly, the present invention relates to an apparatus having articulating arms that support a surgical light, a video camera, and video monitors. The present invention also relates to such an apparatus wherein the articulating arms are inter-changeable between apparatus in different locations and configured to display video images selected from a plurality of video devices.

Video monitors are used in surgical theaters for viewing images such as, for example, images produced from lapyroscopic and endoscopic cameras. These monitors display images placed in a position so that the surgeon can view them during a surgical procedure. These monitors are typically mounted on top of a rolling cart that contains the lapyroscopic or endoscopic equipment. This cart is large and bulky and takes up valuable space around the operating table. Since the monitor is on top of the cart, the monitor cannot always be placed in a position that is the most optimum for viewing by the surgeon.

In many surgical procedures, two monitors are used because a physician's assistant is located on the opposite side of the operating table from the surgeon and cannot see the monitor that is positioned for the surgeon's viewing. In these cases, two monitors must be used at different locations around the table. The positions of the monitors varies depending on the type of surgery and the positions of the surgeon and the assistant. Having two carts with monitors on them takes up an excessive amount of floor space.

With the development of flat screen monitors, the size of the monitors has decreased dramatically. For flat screen monitors and CRT monitors having comparable image sizes, the footprint of the flat screen monitor enclosure is much smaller than that of the comparable CRT monitor. Similarly, the weight of the flat screen monitor is only a fraction of a comparable CRT type monitor.

Flat screen monitors are compatible with mounting on an arm that is attached to the ceiling. This allows the endoscopic cart to be separated from the video monitor. The cart can then be moved away from the table to different areas of the suite out of the way of the surgeon. The scope is plugged into a wall outlet that is hard wired through the wall and down through the support arms to the video monitors.

Filming and recording surgical procedures is now becoming more routine. Operating rooms are typically not adequately equipped to record these surgical procedures. In fact, more often than not, a surgeon employs the services of a professional company or utilizes the in house services available to film a procedure. This requires advance scheduling and is very expensive. Previously, such filming of surgical procedures was principally done for education within the hospital. Today, however, the need to film surgical procedures has expanded considerably.

Cameras are used in operating rooms as a means of networking with the rest of the world. The camera has now become the vehicle by which surgeons can consult with each other during live procedures. For certain surgical procedures it is not uncommon for surgeons to consult with each other from different parts of the world during a case (commonly referred to as 'Telesurgery'). In teaching hospitals, clinical educators require interactive filming capabilities that can be controlled remotely from the classroom. Such procedures are either recorded for critique at a later date or simply observed 'real time' for teaching. Surgeons routinely record procedures and edit the content for presentation at a conference. More surgical procedures are being recorded for future reference should the outcome of the surgery be questioned.

The increased practice of endoscopic and lapyroscopic surgery has produced the need for more sophisticated camera and monitor systems that can alternate between internal and external images. The need to do this in a seamless and user friendly fashion is driving the demand for a new level of sophistication in cameras offered with surgical theater systems. Among the features demanded in these new systems is the ability for the system to be operated by the surgical staff.

Preferably, a surgical camera is movable to different vantage points around the patient, and should even be able to shoot laterally and directly downwardly over the center of the patient. To meet this unique set of needs and provide flexibility, the present invention provides a surgical theater system having a camera mounted on a support arm assembly extending from the same hub which supports the surgical light.

Typically, a surgical light hangs above the table in an OR suite for lighting the surgical site. Many health care facilities have more than one, and often several, OR suites in which surgical lights are mounted to illuminate surgical procedures. The disclosed device includes a plurality of arms mounted to the hub of a surgical theater system so that a surgical light, a camera and/or video monitors can be positioned effectively around the surgical table. In this specification, including the claims, the term "hub" is intended to refer to a member which rotates about an axis or shaft. Typically, a shaft is mounted to the ceiling in the OR to extend downwardly and at least one and often two lights are mounted on the hub for movement about the shaft.

According to one aspect of the present invention, a surgical light apparatus includes a monitor attached to an arm coupled for pivotal movement about a hub assembly configured to be attached to a ceiling and a video input controller electrically coupled to the monitor. The video input controller includes a first channel input having a video coupling for attachment to a first video input device providing a first video feed, a second channel input having a video coupling for attachment to second video device providing a second video feed, and a channel controller coupled to the monitor, first channel input, and second channel input. The channel controller is configured to select a video feed to the monitor. The first channel input may include a plurality of video couplings, and the apparatus may include a first selector to select between the plurality of video couplings as a source of a first video feed. The second channel input may include a plurality of video couplings, and the apparatus may include a second selector to select between the plurality of video couplings as a source of a second video feed. Third and fourth channel inputs providing third and fourth video feeds may also be included. The apparatus may include a second monitor coupled by an arm to the hub assembly, the second monitor being electrically coupled to the channel controller of the video input controller so that channel controller selects a video feed to the second monitor. An output panel may be provided having a first connector coupled to the video feed selected for the first monitor and a second connector directly coupled to one of the first, second, third, and fourth video feeds. A camera may be coupled by a camera arm for pivotal movement about the hub and controlled by a camera controller electrically coupled to the camera arm, the camera controller being located at a remote location from the remainder of the surgical light apparatus.

According to another aspect of the present invention, a surgical light apparatus includes a monitor mounted to a monitor mount attached to an arm coupled for pivotal movement about a hub assembly configured to be attached to a ceiling and a video input controller electrically coupled to the monitor. The handle includes an actuator mounted thereto. The video input controller includes a first channel input having a video coupling for attachment to a first video input device providing a first video feed, a second channel input having a video coupling for attachment to second video device providing a second video feed, and a channel controller coupled to the monitor, first channel input, and second channel input. The channel controller is configured to select a video feed to the monitor in response to actuation of the actuator button. The handle may be sterilizable. The actuator button may include a channel increase and decrease button.

According to yet another aspect of the invention, a surgical light apparatus includes a camera mounted to a camera mount mounted to an arm coupled for pivotal movement about a hub assembly configured to be attached to a ceiling. The camera includes an on/off function, automated zoom capabilities, and automated focus capabilities. The camera mount includes a handle on which an actuator is mounted so that actuation of the actuator controls the on/off function of the camera. The handle may be sterilizable. A second actuator may be mounted on the handle so that actuation of the second actuator controls the zoom capabilities of the camera. A third actuator may be mounted on the handle so that actuation of the third actuator controls the focus capabilities of the camera. The handle may also include a longitudinal axis and be mounted to the remainder of the camera mount for pivotal movement of the handle about the longitudinal axis so that pivotal movement of the handle actuates the second actuator.

Additional features and advantages of the invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description particularly refers to the accompanying figures in which:

FIG. 16 is a perspective view of a surgical theater system having two lights mounted by light arm assemblies for rotation about a hub, and two multipurpose arm assemblies mounted for pivotal movement about pivot joints mounted for rotation about the hub, one multi-purpose arm is shown with a monitor mounted thereto and a camera and monitor configured for coupling to the other multi-purpose arm are shown adjacent the other multi-purpose arm of the apparatus;

DETAILED DESCRIPTION OF THE DRAWINGS

Figure 1:
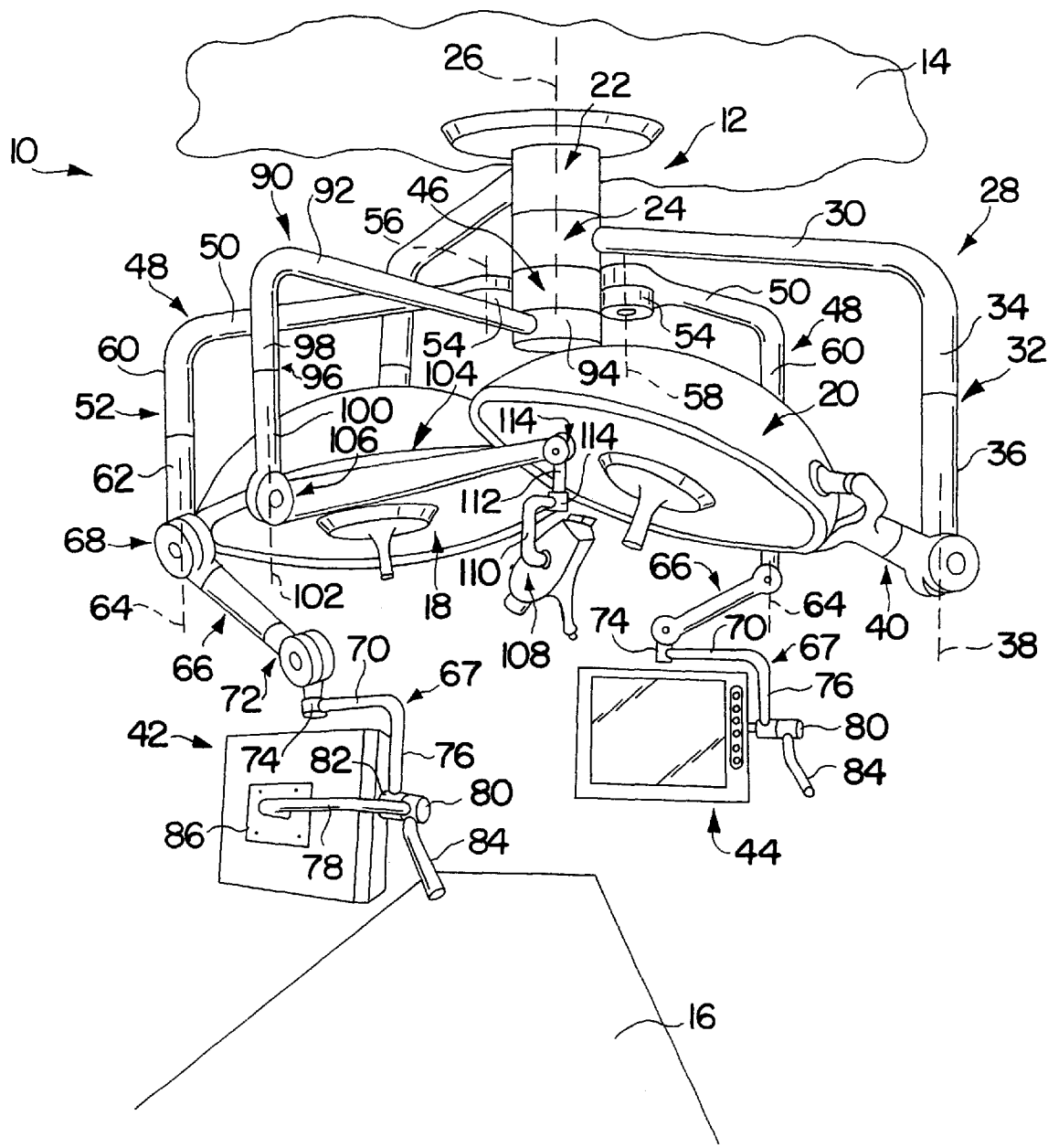
FIG. 1 is a perspective view illustrating a surgical theater apparatus of the present invention, including first and second surgical lights mounted to a central hub, first and second monitors coupled to support arms attached to the central hub, and a camera coupled to a support arm attached to the central hub.

Referring to the drawings, several embodiments of a surgical theater system 10 and controls for a surgical theater system are illustrated. Each surgical theater system embodiment illustrated includes a central hub 12 composed of a plurality of hub portions. One hub portion, referred to as connection hub or monitor hub 46, or connection hub or multi-purpose hub 646, of each illustrated embodiment is adapted for mounting of two arms thereto. The connection hub 46 and 646 is configured to facilitate mounting two arms to a surgical theater system in less vertical area than is typically required for mounting two arms using standard hub configurations. This configuration allows more devices to be mounted to a central hub of a surgical theater system with minimal intrusion into the head space available for the surgical staff over the operating table. The other hub portions are of standard configuration and are of the type by which surgical lights, cameras, and or monitors are typically mounted to the central hub of a surgical theater system. It is understood that the central hub 12 may include a plurality of connection hubs 46 and 646 within the teaching of the present invention. While the surgical theater systems are illustrated having configurations with a specific number of surgical lights, cameras, and/or monitors, it is within the teaching of the disclosure as presently perceived for different configurations of surgical light heads, monitors, and/or cameras to be included in each described surgical theater system.

FIGS. 1–4 illustrate two embodiments of a surgical theater system 10 having two dedicated light arms, a dedicated camera arm 90, and two dedicated monitor arm assemblies 48 and 180 attached to a hub 12. Both embodiments of the monitor arm assembly 48 and 180 include a bent upper arm having a horizontal arm 50 and a vertical arm 52 having an upper section 60 and a lower section 62, a laterally-extending arm 66 and 188 coupled to the lower section 62 of the bent arm, and a lower assembly or mount 67 coupling the monitor 42 and 44 to the laterally-extending arm 66 and 188. The two embodiments differ in the type of arm used for the laterally-extending arm 66 and 188 and the manner in which the laterally-extending arm 66 and 188 is coupled to the bent arm and the lower assembly 67. Thus, the similar components of the two embodiments of monitor arm assembly 48 and 180 will be discussed with regard to the adjustable counterbalanced arm assembly 48 with the understanding that the fixed height monitor arm assembly 180 is similarly fashioned. Any slight differences between the two embodiments will be indicated. However, each laterally-extending arm embodiment 66 and 188 will be discussed separately.

Figure 2:
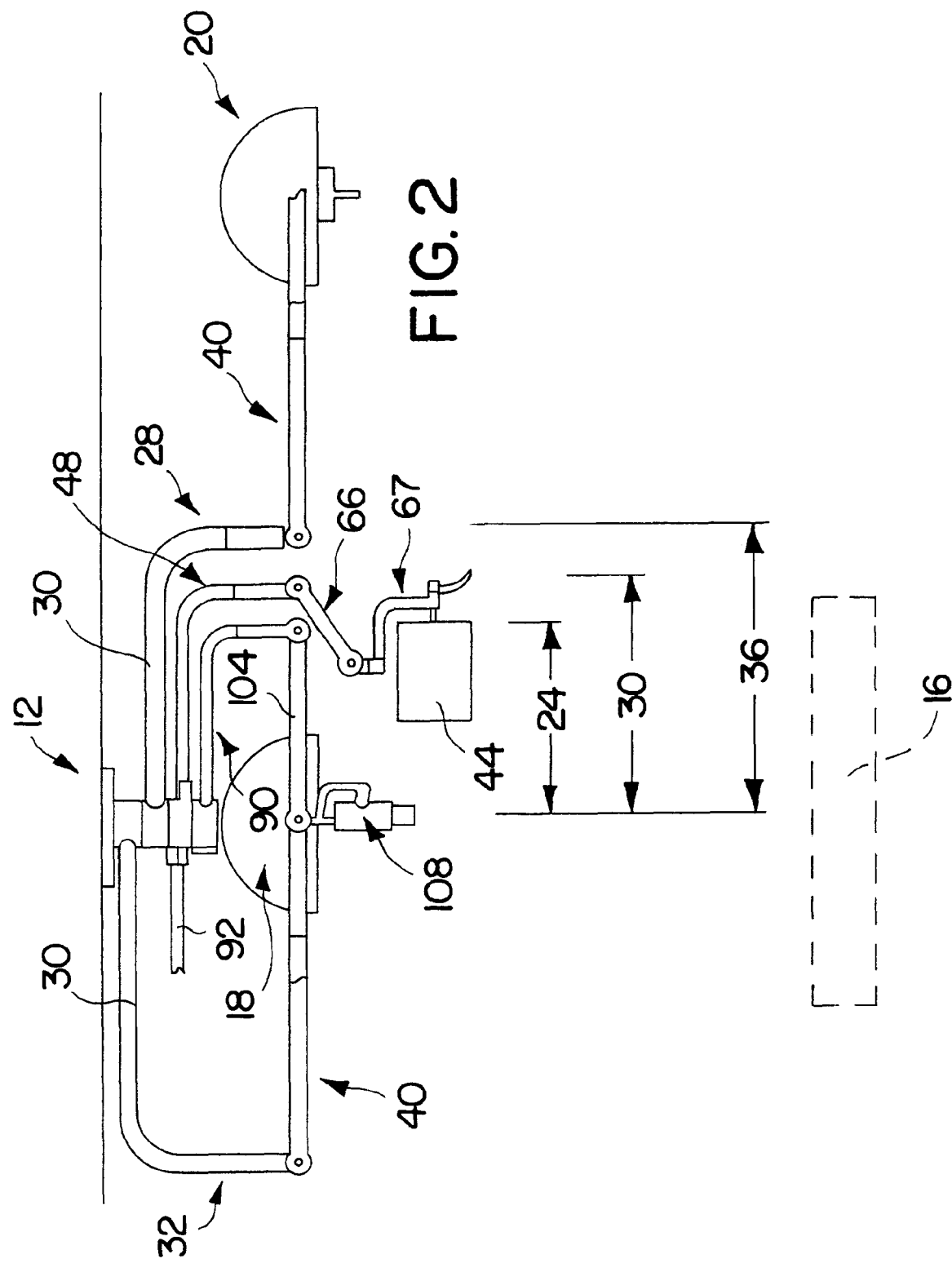
FIG. 2 is a side view illustrating positions of all the support arms attached to the central hub.
Figure 3:
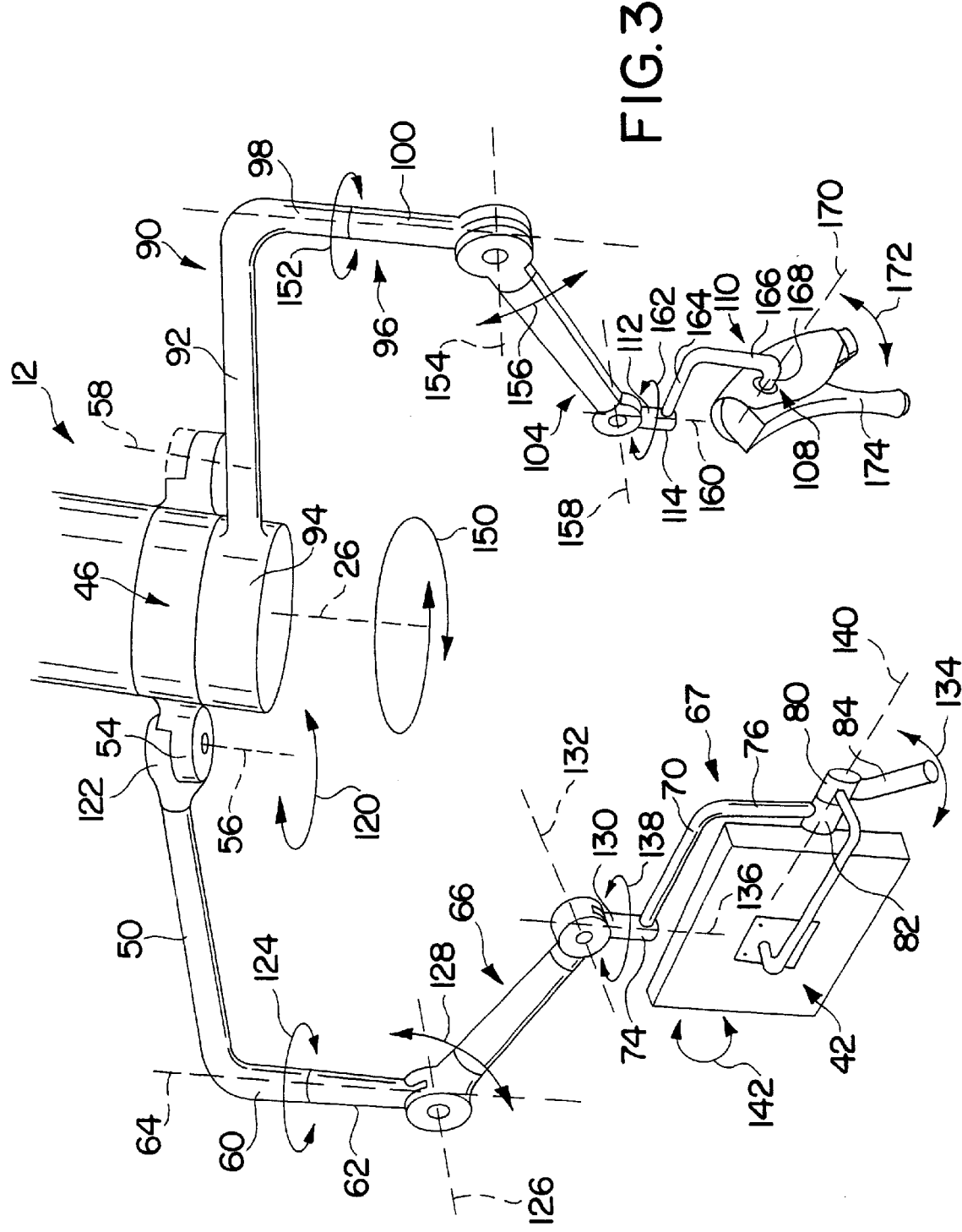
FIG. 3 is a perspective view illustrating movement of an adjustable height monitor arm assembly and the camera arm assembly.

Referring now to the drawings, FIGS. 1–3 illustrate a surgical theater system 10 according to one aspect of the present invention. The surgical theater system 10 includes a central hub 12 mounted to support 11 mounted to a ceiling 14 in a room such as a surgical suite. The hub 12 is located over an operating room table 16 or other patient support device on which a surgical procedure is to be performed. First and second surgical lights 18 and 20 are pivotally coupled to first and second light hubs or hub sections 22 and 24, respectively, of hub 12 by light arms or support arm assemblies 28. Therefore, the surgical lights 18 and 20 are rotatable about axis 26 of hub 12.

Surgical light support arms 28 include horizontally extending sections and vertically extending sections 32. Vertically extending arm sections 32 include upper and lower sections 34 and 36 so that the vertical sections 32 are rotatable about axis 38. A counterbalanced arm 40 is pivotally coupled to vertical arm section 32 for supporting surgical lights 18 and 20. In each of the illustrated embodiments of a surgical theater system, the light heads, light arms and light hubs are of the type commonly used in surgical theater systems including only light heads and light arms. Details of the surgical lights 18 and 20 and surgical light support arms 28 are disclosed in U.S. Pat. Nos. 6,012,821 and 6,132,062 and U.S. applications Ser. Nos. 09/050,265; 09/050,529; and 09/050,534 which are expressly incorporated herein by reference.

In the FIG. 1–4 embodiments of the surgical theater system 10, dedicated monitor arms 48 and 180 are mounted to a monitor hub 46 forming a portion of the central hub 12. Each of the two monitor arm assemblies 48 and 180 of each embodiment is coupled through top pivot joint 122 to a respective bottom pivot joint 54 permitting each monitor arm assembly 48 and 180 to swivel through a range of about 180° around its associated pivot axis 56 and 58 extending through its associated pivot joint 54. The rotation of the monitor hub 46 to which each monitor arm assembly 48 and 180 is coupled allows each monitor 42 and 44 to be placed anywhere around the surgical table. Each monitor arm assembly 48 and 180 may move about its respective pivot axis 56 and 58 without inducing rotation of the monitor hub 46 about rotation axis 26 until the top pivot joint 122 to which arm assembly 48 and 180 is attached hits a stop. Thus, a 180° movement of one arm assembly between its first stop limit and its second stop limit occurs without creating movement in the other monitor arm assembly coupled to connection hub 46. Once one arm assembly is moved in a direction until top pivot joint 122 to which it is attached hits the stop, additional movement of that arm assembly in the same direction causes the other arm assembly to rotate as well because the entire connection hub 46 rotates.

The vertical arm 52 of the bent arm of each monitor arm assembly 48 and 180 extends downwardly from the horizontal arm 50 at a location radially inwardly from vertical sections 32 of the light arms 28. Upper section 60 and lower section 62 of vertical arm 52 are coupled by a swivel mechanism including a slip ring assembly permitting the lower section 62 to rotate about a rotation axis extending through the upper section 60. The laterally-extending arm, coupled to the monitor 42 and 44 through the lower assembly, also rotates about the rotation axis extending through the upper section 60 to permit the monitor to be placed closer to or farther away from the vertical arm 52.

In the fixed height monitor arm assembly 180, the laterally-extending arm 188 is one portion of a unitary off-set or S-shaped section 182 also including an upper section 184 and a lower arm section 190. Upper arm section 184 replaces lower section 62 of vertical arm 52 of arm assembly 48 so that upper arm section 184 is pivotally mounted to upper section 60 of vertical arm 52. Laterally-extending or horizontal arm section 188 of arm assembly 180 is also rigidly mounted to the lower assembly 67. For uniformity in description, while physically a component of off-set or S-shaped section 182, lower arm section 190 is functionally a component of lower assembly 67 in arm assembly 180. The laterally-extending or horizontal arm 188 of the fixed height monitor arm assembly 180 includes an offset of about 14" to allow the monitor to reach beyond the head or foot of the table and to be placed even with the side of the table.

In the adjustable height monitor arm assembly 48, counterbalanced arm 66 is attached to the vertical arm 52 illustratively at about a 78" height above the floor. This counterbalanced arm 66 contains a parallelogram link that keeps the monitor 42 and 44 in a consistent orientation relative to the floor when it is raised upwardly or lowered downwardly.

Referring again to both embodiments of monitor arm assembly 48 and 180, the lower assembly 67 extends from below the laterally-extending arm 66 and 188. Below the connection point of the laterally-extending arm 66 and 188 to the lower assembly 67, the lower assembly 67 includes another swivel including a slip ring that allows monitor 42 and 44 to be rotated to position the monitor at the desired viewing angle. Attached to this arm is a bracket 86, 196 that attaches to the monitor and allows the monitor to tilt to eliminate glare and improve viewing angle. A sterile handle 84, 194 is coupled to the back of the monitor-attaching bracket 86, 196 to aid in moving the monitor to its desired position. All cables for video monitor 42 and 44 and camera 108 are substantially enclosed inside the articulating arms 48, 180, and 90.

As further illustrated in FIG. 1, first and second monitors 42 and 44 are coupled to the central hub 12. Illustratively, monitors 42 and 44 are Model LC150M2 monitors available from Sharp or Model SH46/H746 monitors available from Computer Dynamics Inc. It is understood that any suitable monitors may be used. Monitors 42 and 44 are coupled to connection hub or monitor hub 46 by support arm assemblies 48. Illustratively, a monitor support arm assembly 48 includes a bent arm or first segment having a horizontal arm section 50 and a vertical arm section 52 for each monitor 42 and 44. Horizontal arm sections 50 are coupled to bottom pivot joints 54 which extend away from a main hub section 47 of connection hub 46. Therefore, the horizontal arm sections 50 are pivotable about pivot axes 56 and 58 which are spaced apart from the pivot or rotation axis 26 of central hub 12.

Vertical arm sections 52 of monitor arm assemblies 48 illustratively each include first or upper section 60 and second or lower sections 62. The second vertical section or extension arm 62 is rotatable relative to the first vertical section 60 about axis 64. In monitor arm assembly 48, counterbalanced arm 66 is pivotally connected at its proximate end to second vertical section 62 by a pivot connection 68 having an upwardly extending mounting shaft 346. Counterbalanced arm 66 is pivotally mounted about pivot connection 72 at its distal end to a lower assembly 67. Pivot connection 72 includes a downwardly extending mounting shaft 358.

In monitor arm assembly 48, lower assembly 67 includes horizontal arm 70, hub or arm 74, vertical arm 76, monitor mounting arm 78, hub 82, handle 84, and monitor support plate 86. Horizontal arm 70 is coupled at its distal end to downwardly extending mounting shaft 358 of pivot connection 72. Mounting shaft 358 is rotatably mounted to a lower arm section or hub 74 of a lower mounting assembly 67. Vertical arm 76 is coupled to horizontal arm section 70. Monitor mounting arm 78 has a first end 80 rotatably coupled to a hub 82 of vertical arm 76. Handle 84 is coupled to end section 80. A second end 85 of mounting arm 78 is coupled to a monitor support plate 86. Movement of the monitor arm assemblies 48 is described in detail with reference to FIG. 3 discussed below.

As shown, in FIGS. 1–4 the surgical theater system includes a dedicated camera hub to which a camera is mounted by a camera arm. The dedicated camera hub is mounted for movement about the downwardly extending shaft of the surgical theater system. The hub allows for 360° rotation so the camera is movable anywhere over the table without obstruction. This is done by using a slip ring design electrically coupling a first cable carried by the shaft to a second cable carried by an arm that couples the camera to the hub. The slip ring, first cable and second cable carry video signals between the camera and a monitor, and electrical power from a power supply to the camera.

The camera has a sterile handle that can be grabbed to move the camera to any position around the table. With this handle, the camera can be pointed at the surgical site with feedback from the monitor. In an illustrated embodiment of controls for a surgical theater system, a remote control (wired or wireless) is used to make fine adjustments to pan, tilt, rotate and zoom. A wall remote control can also be used to control the camera. These controls can also be operated from a remote location such as in a conference room for observers.

Accordingly, the surgical theater system 10 further includes a camera mounting arm assembly 90 having a horizontal arm section 92 coupled to camera hub 94 of central hub 12. A vertical arm section 96 is coupled to horizontal arm section 92. Vertical section 96 includes a first, upper section 98 and a second, lower arm section 100 rotatably coupled to arm section 98 about axis 102. A counterbalanced arm 104 is coupled to lower vertical section 100 by a pivot connection 106. A camera 108 includes a camera mounting arm 110 rotatably mounted on shaft 112 by hub 114. Shaft 112 is pivotally connected to counterbalanced arm 104 by pivot connection 116. Illustratively, camera 108 is a Model DXC970MD available from Sony. It is understood that any suitable camera may be used.

Camera arm assembly 90 is mounted to hub section or camera hub 94. Hub section 94 is rotatable about axis 26 as illustrated by double-headed arrow 150. Lower vertical arm section 100 is rotatable about axis 102 relative to upper vertical section 98 as illustrated by double-headed arrow 152. Counterbalanced arm 104 is pivotable relative to vertical arm section 96 about pivot axis 154 as illustrated by double-headed arrow 156. Shaft 112 is pivotally mounted to the other end of counterbalanced arm 104 about pivot axis 158. In addition, mounting arm 110 is rotatably mounted to shaft 112 by hub 114 about axis 160 as illustrated by double-headed arrow 162. The illustrated arm 110 includes a horizontal arm section 164 rigidly mounted to hub 114, a vertically extending arm section 166, and a horizontally extending coupling arm 168 coupled to camera 108. Camera 108 is rotatable about axis 170 as shown by double-headed arrow 172. Handle 174 is provided for moving and controlling the camera 108.

Electrical cables are routed through arm assemblies 48 and 90 through hub 112 to other equipment within the hospital room or connected to a remote location through an electrical communication network. In the illustrated embodiment, camera arm assembly 90 is very similar to monitor arm assembly 48, differing significantly from the monitor arm assembly 48 only in the type of hub to which it is mounted at its proximate end, the electrical cables routed therethrough, and the type of lower mounting assembly coupled to the distal end of the counterbalanced arm.

The spacing and relative position of the arm assemblies 28, 48, and 90 are illustrated in FIG. 2. The arms are spaced radially inwardly from each other so that each arm can rotate 360° around central hub 12. The surgical lights 18 and 20 can, therefore, be placed at any desired location relative to the operating table 16. In addition, the camera 108 can be moved to desired locations including directly over the top of the surgical table 16 as shown in FIG. 2.

FIG. 3 illustrates movement of the monitor arm assemblies 48 and the camera arm assembly 90 of FIG. 1. As discussed above, the horizontal sections 50 of monitor arm assemblies 48 are pivotable about axes 56 and 58 of bottom pivot joints 54 of connection hub 46 as illustrated by double-headed arrow 120. Stops are provided on bottom pivot joints 54 and top pivot joints 122 attached to each horizontal arm section 50. Illustratively, the horizontal arm sections 50 pivot about 180° relative to bottom pivot joint 54. As is described further below, once a stop on top pivot joint 122 engages a stop on bottom pivot joint 54, further movement of monitor arm 50 causes the entire connection hub 46 to rotate. Therefore, after the first monitor arm is rotated 180°, further rotation causes the first monitor arm and the other monitor arm to rotate with connection hub 46.

Lower vertical section 62 of arm assembly 48 is rotatable relative to upper vertical section 60 as illustrated by double-headed arrow 124, as shown, for example, in FIG. 3. Counterbalanced arm 66 is pivotable about axis 126 as illustrated by double-headed arrow 128. Shaft 130 is pivotally mounted to pivot connection 72 about axis 132. Therefore, the operator can pivot the monitor 42 about axis 132 by moving handle 84 as shown by double-headed arrow 134. Hub 74 is rotatable on shaft 130 about axis 136 as illustrated by double-headed arrow 138. Mounting arm 78 is also rotatable relative to hub 82 about axis 140 as illustrated by double-headed arrow 142.

Figure 5:
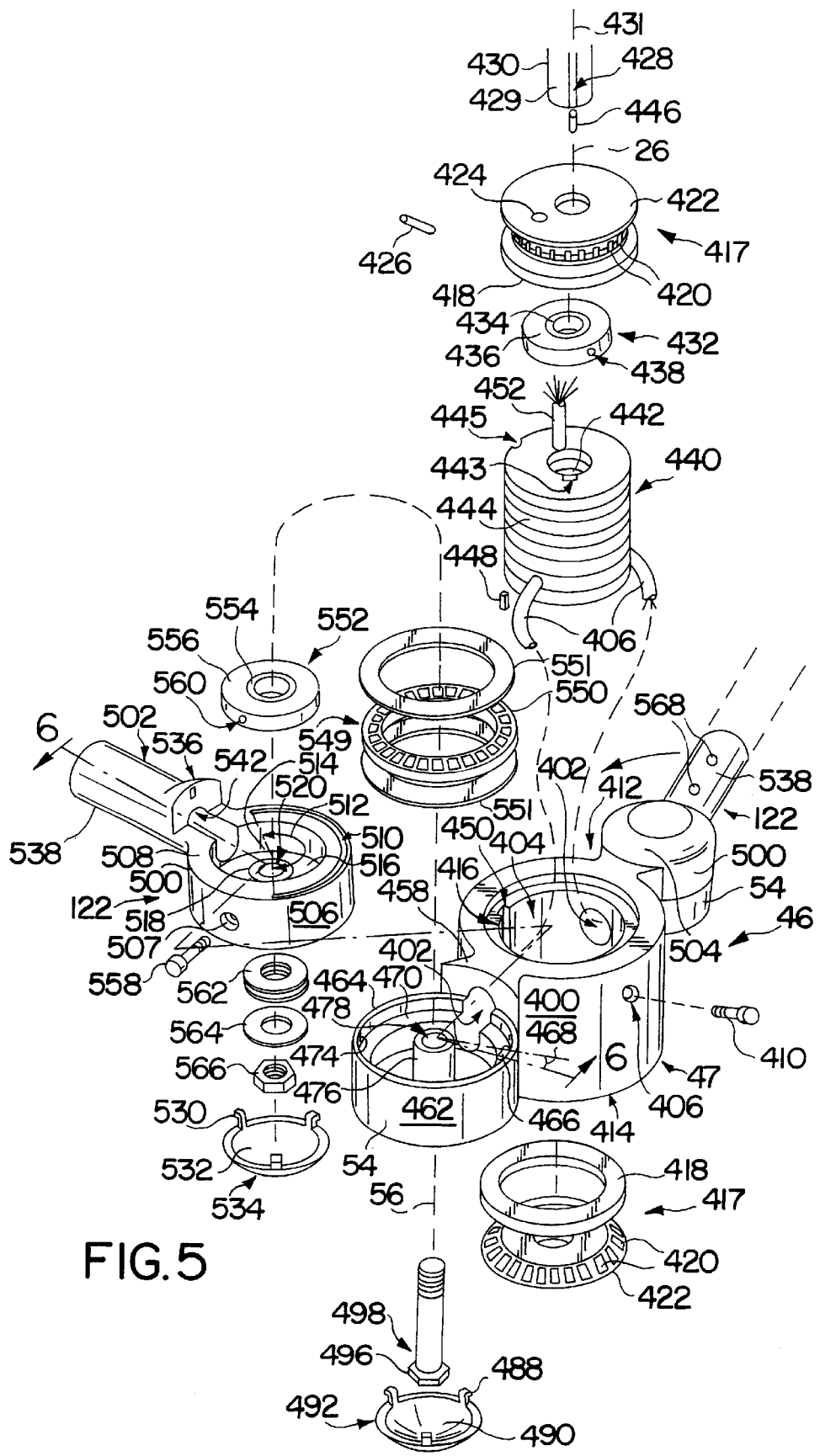
FIG. 5 is an exploded view of a monitor connection hub section of the central hub of FIGS. 1 and 4, showing the monitor hub including a main hub and two radially extending lower pivot joints and two upper pivot joints, and showing the various components received in the main hub and pivot joints.
Figure 6:
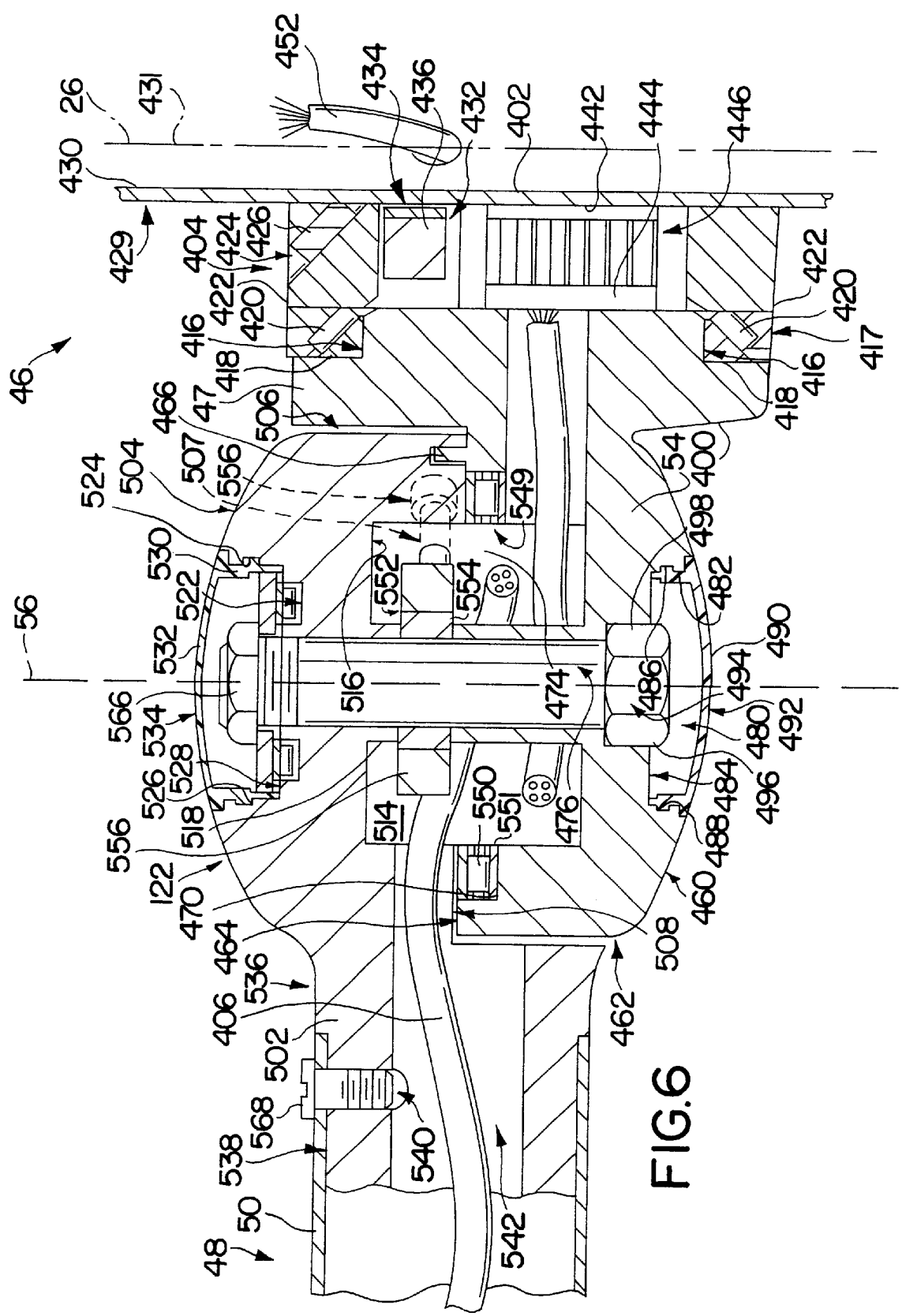
FIG. 6 is a sectional view taken along line 6—6 of FIG. 5 of an assembled main hub and pivot joint.
Figure 7:
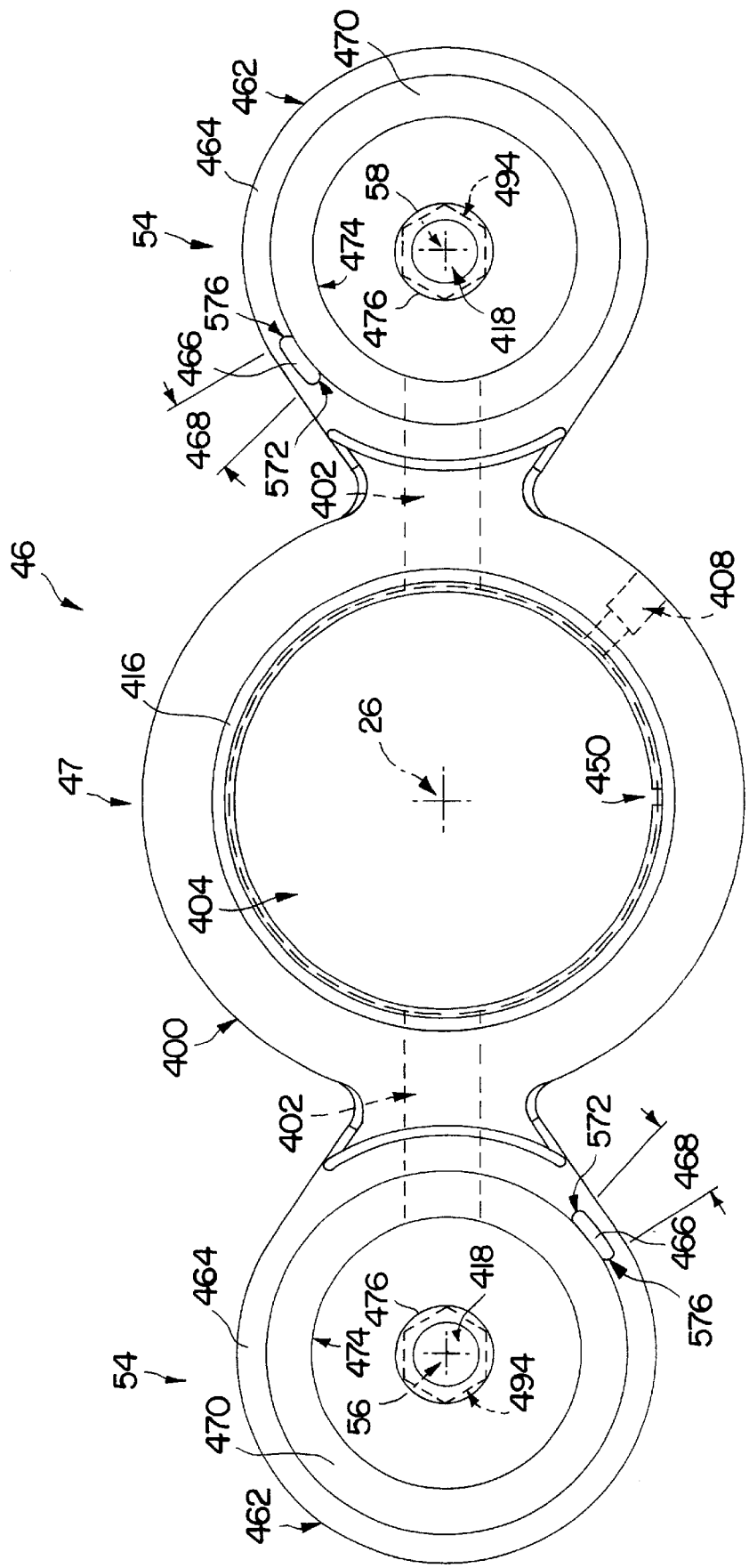
FIG. 7 is a plan view of the monitor connection hub of FIG. 5 showing an arcuate stop extending upwardly from the bottom pivot joint.
Figure 8:
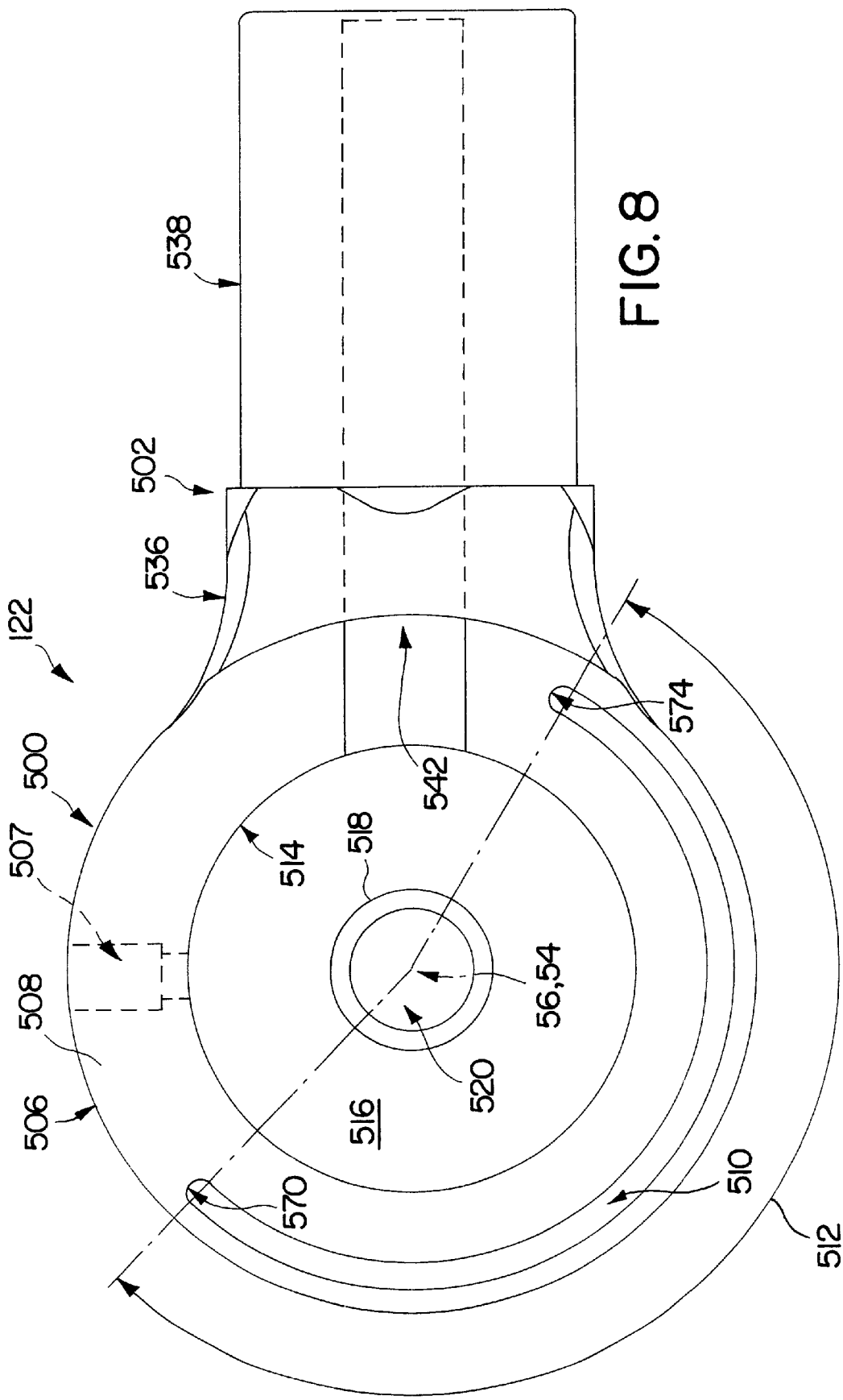
FIG. 8 is a bottom view of the top pivot joint of FIG. 5 showing an arcuate slot sized to receive, and cooperate with, the arcuate stop of FIG. 7 to limit pivotal movement of the monitor support arms.
Figure 9:
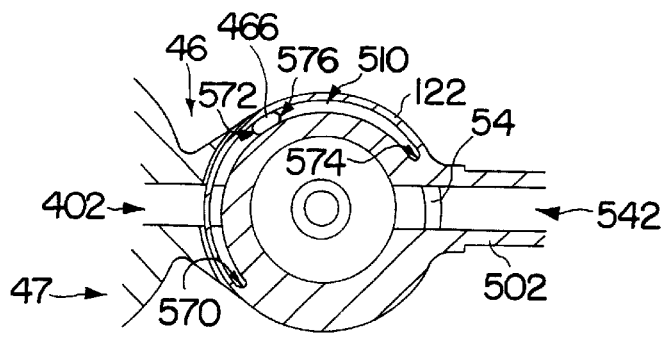
FIG. 9 is a sectional view taken along line 9—9 of FIG. 1 showing the arcuate stop extending upwardly from the bottom pivot joint received in the arcuate slot of the top pivot joint (shown in section) and showing a pivot arm section of the top pivot joint extending radially from the main hub.

As described above, and as shown more particularly in FIGS. 5–7, connection hub 46 includes a main hub section 47 and two diametrically opposed bottom pivot joints 54 extending radially beyond outer surface 400 of main hub section 47. In the illustrated embodiment, outer surface 400 of main hub section 47 is a cylindrical surface concentric about rotation axis 26. Main hub section 47 is formed to include an interior bore 404. Interior bore 404 is concentric about rotation axis 26.

Main hub section 47 is substantially similar to a standard hub section for surgical lights with a few significant differences. Besides the obvious difference of having two diametrically opposed bottom pivot joints 54 formed integrally therewith instead of a single support arm connector, main hub section 47 includes two, instead of one, radially extending holes 402 communicating between interior bore 404 and bottom pivot joints 54. Main hub section 47 also includes a radially extending counter-bored hole 408 for receipt of a brake adjustment screw 410.

Radial holes 402 are provided to permit passage of cables 406 containing wires for power, ground, video signals, and shield ground. In the illustrated embodiment, cables 406 contain four wires, i.e. a ground wire, a wire carrying electricity at 12 volts above the potential of ground wire, a shielded cable carrying a C video signal, and a shielded cable containing a Y video signal. Different C and Y video signals can be provided to each different monitor.

A pair of bearing assemblies 417 each include a first tapered race 418, a second tapered race 422, and a plurality of caged rolling elements 420 positioned therebetween. Near top 412 and bottom 414 of main hub section 47, interior bore 404 is counter bored to form a shoulder 416 for receipt of first tapered race 418 on which rolling elements 420 run. Second tapered race 422 is formed to include a hole 424 through which a lock pin 426 is inserted to stake race 422 to shaft 430. Shaft 430 has this longitudinal axis of symmetry 431 on rotation axis 26 which is illustratively concentric with longitudinal axis of symmetry of hub 46. Rolling elements 420 of bearings run on both tapered race 422 fixed to shaft 430 and tapered race 418 held on shoulder 416 of main hub section 47 to allow main hub section 47 to rotate about rotation axis 26.

The ease with which connection hub 46 rotates about rotation axis 26 can be set by the user or assembly technician through adjustment of brake assembly 432. Brake assembly 432 includes a brake pad 434, metal cylindrical sleeve 436, and brake adjustment screw 410. Illustratively, brake pad 434 is in the form of a Rulon® bushing. (Rulon® is a registered trademark of Dixon Corporation). Brake pad 434 is press fit into metal cylindrical sleeve 436 which is formed to include a tapped hole 438. Shaft 430 extends through Brake pad 434. Brake adjustment screw 410 extends through counter bored hole 408 in main hub section 47 and is received in tapped hole 438. Tightening and loosening of adjustment screw 410 causes the frictional force exerted by Brake pad 434 on shaft 430 to be increased and decreased respectively. Preferably, these frictional forces are set so that monitor arm assemblies 48 can pivot through their full range about pivot axes 56 and 58 without inducing rotation of connection hub 46 about rotational axis 26. Once monitor arms 48 have reached their limits, further rotation of monitor arm 48 will induce rotation of the entire connection hub 46 about rotational axis 26.

Connection hub 46 is adapted to provide power and video signals to monitors 42 and 44. To facilitate power and signal transmission to monitors 42 and 44, connection hub 46 includes slip ring assembly 440. Slip ring assembly 440 is illustrated diagrammatically, the actual internal construction being well known. Slip rings 440 are commercially available from Litton Systems, Inc., Blacksburg, Va., and are known in the art. Slip ring assembly 440 includes an inner plastic sleeve 442, outer plastic sleeve 444, two four-wired cables 406, and a six-wire cable 452. Inner plastic sleeve 442 is formed to include a keyway 443 to receive key 446 which is also received in keyway 428 formed in outer surface 429 of shaft 430 to couple inner sleeve 442 to shaft 430. Six-wire cable 452 runs through the interior shaft 430. Outer plastic sleeve 444 is formed to include a keyway 445 for receipt of a key 448 which is also received in keyway 450 formed in interior bore 404 of connection hub 46 to fix outer sleeve 444 to connection hub 46.

Internally, slip ring assembly 440 includes seven mutually insulated sets of slip rings. The first set of slip rings is coupled to a ground wire in six-wire cable 452 and a ground wire in each of four-wire cables 406. A second set of slip rings is connected to a wire carrying electricity at 12 volts above the potential of ground in six-wire cable 452 and in both four-wire cables 406. The third set of slip rings is connected to a shielded wire carrying the C video signal for monitor 42 in the six-wire cable 452 and in the four-wire cable 406 running to monitor 42. A fourth set of slip rings is coupled a shielded wire carrying the Y video signal for monitor 42 in six-wire cable 452 and the four-wire cable 406 running to monitor 42. A fifth set of slip rings is coupled to a shielded cable carrying the Y video signal for monitor 44 in six-wire cable 452 and the four-wire cable 406 running to monitor 44. A sixth set of slip rings is coupled to the shielded wires carrying the Y video signal for monitor 44 in six-wire cable 452 and the four-wire cable 406 running to monitor 44. A seventh set of slip rings is coupled to the shields for all of the shielded cables in six-wire cable 452 and four-wire cable 406 to provide a shield ground for all of the video signals.

In the illustrated embodiments, bottom pivot joints 54 are integrally formed with main hub section 47 in connection with flange 458 to form connection hub 46. Each bottom pivot joint 54 includes a convex bottom wall 460, a cylindrical outer wall 462, and a flat top wall 464. An arcuate-shaped stop 466 extends upwardly from flat top wall 464. Each cylindrical outer wall 462 is concentric about a respective pivot axis 56 and 58. Each arcuate stop 466 extends upwardly from flat top wall 464 and radially 15° about flat top wall 464, as shown by angle 468 measured from a respective pivot axis 56 and 58 in FIG. 7.

Flat top wall 464 is milled inwardly from arcuate stop 466 to form a shoulder 470. Bottom pivot joint 54 is also formed to include a upwardly opening interior cavity 72 defined by cylindrical inner walls 474 and cylindrical post 476. Each cylindrical post 476 is concentric about a respective pivot axis 56 and 58. An axial bore 478, coaxial with a respective pivot axis 56 and 58, extends through cylindrical post 476 and convex bottom wall 60.

A large counter bore 480, coaxial with a respective pivot axis 56 and 58, is formed in convex bottom wall 460. Counter bore 480 is defined by side wall 482 and wall 484. A radially extending slot 486 is formed in side wall 482 to receive snap legs 488 extending from convex body 490 of cap 492. A hexagonal bolt head-shaped hole 494 is formed in each wall 484 concentric about a respective pivot axis 56 and 58 to receive the head 496 of a hex bolt 498 to prevent hex bolt 498 from rotating with respect to bottom pivot joint 54. Each hex bolt 498 acts as a pivot pin and is concentric about a respective pivot axis 56 and 58. As shown, for example, in FIG. 6, cylindrical post 476 extends slightly upwardly beyond flat top wall 64.

As shown, for example, in FIGS. 5, 6, and 8–10, a top pivot joint 122 is pivotally coupled to each bottom pivot joint 54. Top pivot joint 122 includes a housing 500 and an arm connection section 502. Housing 500 includes a convex top wall 504, a cylindrical side wall 506 and a flat bottom wall 508. An arcuate slot 510 is formed in flat bottom wall 508 and extends around flat bottom wall by an angle 512 measured from a respective pivot axis 54, 56 of approximately 195° as shown, for example, in FIG. 8. Substantially inwardly from arcuate slot 510, flat bottom wall 508 is counter bored to form an inner cylindrical wall 514 and a wall 516. A counter bored hole 507 extends through cylindrical side wall 506 and inner cylindrical wall 514. A cylindrical post 518 extends downwardly from wall 516. Inner cylindrical wall 514 and cylindrical post 518 are concentric about a respective pivot axis 56 and 58. As shown, for example, in FIG. 6 inner cylindrical wall 514 of top pivot joint 122 has substantially the same diameter as cylindrical inner wall 574 of bottom pivot joint 54. An axial bore 520, coaxial with a respective pivot axis 56 and 58, extends through cylindrical post 518 and convex top wall 504.

Convex top wall 504 is bored to form a shoulder 522 concentric about a respective pivot axis 54 and 56. An additional larger but shallower counter bore extends from convex top wall and is defined by step 526 and side wall 524. A channel 528 is formed in side wall 524 to receive snap legs 530 extending from the convex body 532 of a cap 534.

Arm connection section 502 includes a larger diameter tapered section 536 which decreases in diameter as it extends from cylindrical side wall 506 of housing 500 and a small diameter cylindrical section 538. Arm connection section 502 extends radially from housing 500. Small diameter cylindrical section 538 is formed to include threaded holes 540 to facilitate coupling sleeve of horizontal arm 50 onto arm connection section 502. A wire bore 542 extends radially through inner cylindrical wall 514 of housing 500 and arm connection section 502.

During assembly of top pivot joint 122 to bottom pivot joint 54, bearings 549, formed from caged rolling elements 550 sandwiched between two thrust washers 551, are placed on shoulder 470 of bottom pivot joint 54. Hex bolt 498 is inserted through axial bore 478 until head 496 is received in hexagonal hole 494. A brake assembly 552 including a a brake pad 554 in the form of a Rulon® bushing received in a metal cylindrical sleeve 556 and an adjustment screw 558 is attached to the shaft of hex bolt 498. Four-wire cable 406 is routed through hole 402, wrapped around cylindrical post 476 two times and then routed through wire bore 542 in top pivot joint 112. Top pivot joint 112 is then inserted over hex bolt 498 so that hex bolt 498 extends through axial bore 520. Adjustment screw 558 is inserted through counter bored hole 507 in cylindrical side wall 506 so that its threads are received in a threaded hole 560 in metal cylindrical sleeve 556. Arcuate stop 466 is received in arcuate slot 510 and flat bottom wall 508 rests on thrust washer 551 of the bearings. Caged needle rolling elements and two thrust washers form a thrust bearing 562 which is inserted to ride between shoulder 522 and a thrust washer 564. Nut 566 is attached to bolt 498.

Cap 492 is inserted in bottom pivot joint 54 so that snap legs 488 are received in slot 486. Cap 534 is attached to top pivot joint 122 so that snap legs 530 are received in channel 528. Screws 568 are inserted through sleeve of arm and threaded holes 540 in arm connection section 502 to couple monitor arm 48 to connection hub 46. Brake assembly 552 is adjusted by tightening or loosening adjustment screw 558 to increase or decrease the frictional force exerted by Brake pad 554 on hex nut 498. Preferably, brake assembly 552 is adjusted so that top pivot joint 122 pivots more easily about pivot axis 56 and 58 than connection hub 46 rotates about rotation axis 26.

Figure 10:
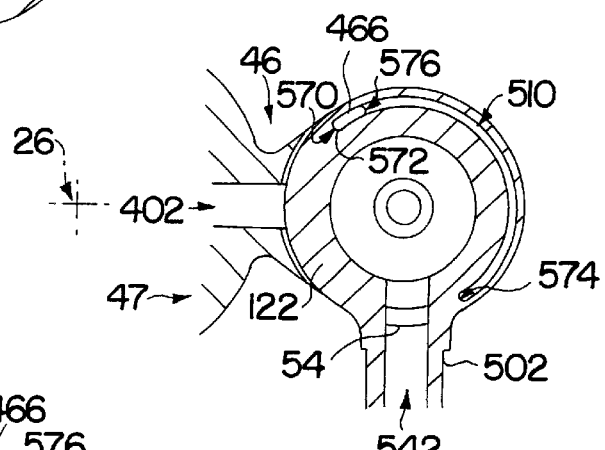
FIG. 10 is a sectional view similar to FIG. 9 showing the top pivot joint pivoted 90 degrees in a first direction until the stop has engaged a first end of the arcuate slot with such movement occurring without inducing rotation of the hub about its rotational axis.
Figure 11:
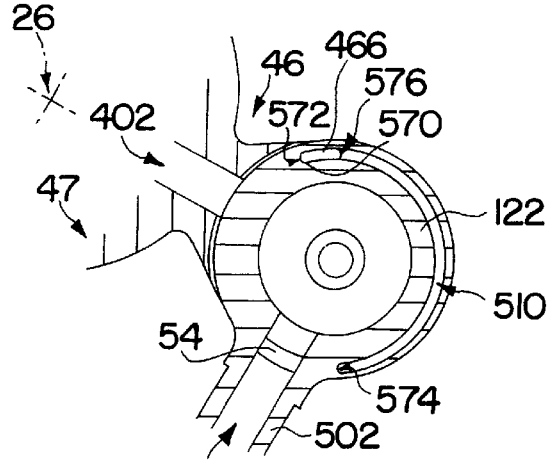
FIG. 11 is a sectional view similar to FIG. 10 showing the hub rotated in the first direction as a result of additional force being exerted in the first direction on the top pivot joint after the arcuate stop engaged the first end of the arcuate slot.
Figure 12:
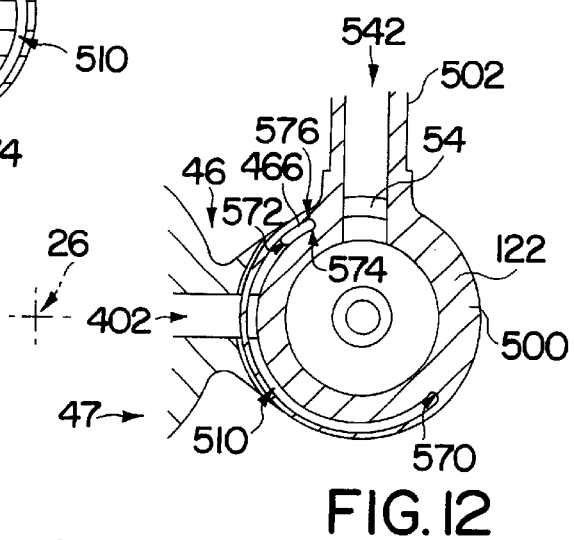
FIG. 12 is a sectional view similar to FIG. 9 showing the top pivot joint pivoted 90 degrees in a second direction until the arcuate stop has engaged a second end of the arcuate slot.
Figure 13:
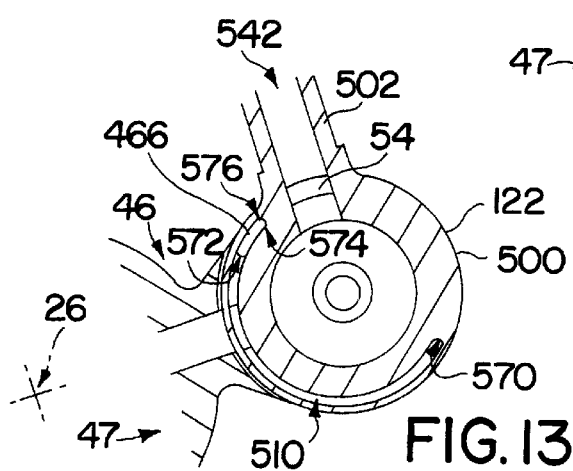
FIG. 13 is a sectional view similar to FIG. 12 showing the hub rotated in the second direction as a result of additional force being exerted in the second direction on the top pivot joint after the arcuate stop engaged the second end of the arcuate slot.

As shown, for example, in FIGS. 9–13, in the illustrated embodiment, each top pivot joint 122 pivots about a respective pivot axis 56 and 58 approximately 180° between a first limit in which first end 570 of arcuate slot 510 is contacted by first side 572 of arcuate stop 466 (shown in FIG. 10) and a second limit position wherein second end 574 of slot 510 is engaged by second side 576 of arcuate stop 466 (shown in FIG. 12). As shown, for example, in FIGS. 9, 10, and 12, if brake assemblies 552 and 432 are adjusted in a preferred manner, pivoting of either monitor arm 48 (not shown in FIGS. 9–13) attached to arm connection section 502 between the first limit position and the second limit position will not induce rotation of connection hub 46 about rotation axis 26. After monitor arm 48 has been rotated in a direction until it reaches a limit position, as shown by FIGS. 10 and 12, further rotation of the monitor arm 48 in the same direction will induce rotation of connection hub 46 about rotation axis 26, as shown, for example, in FIGS. 11 and 13.

Counterbalanced arms 66, 104 are pivotable arms bearing loads, shown as monitors 42 and 44 and camera 108. Counterbalanced arms 66, 104, like typical counterbalanced arms, include spring mechanisms which act as counterbalances to the load carried at the end of the arm opposite the pivot point. One problem experienced with counterbalanced arms is that after the counterbalanced arm has been pivoted so that its load is at the desired height, the weight of the load may induce the arm to pivot downwardly slightly after it is released. This unwanted travel is typically the result of the spring mechanism being improperly tensioned. Counterbalanced arms 66, 104 are designed to reduce this unwanted travel. Counterbalanced arm 66 will be described hereafter, it being understood that counterbalanced arm 104 is similarly constructed.

Counterbalanced arm 66 includes a first plastic housing half 210, a second plastic housing half 212, and an arm assembly 214. First housing half 210 is joined to second housing half 212 to enclose arm assembly 214 to provide an easily cleanable outer surface and to prevent particulate matter and fluids from interfering with the mechanisms of arm assembly 214. It is within the scope of the disclosure to house the structural elements of the counterbalanced arm 66 within other appropriate enclosure including a cast aluminum one piece enclosure.

Arm assembly 214 includes a load bracket 216, an upright bracket 218, a first gas cylinder 220, a second gas cylinder 222, a bottom box C-shaped link 224, a top box C-shaped link 226, a counterarm 228, a counterarm bracket 230, a slide pin 232, a counterarm bracket adjustment screw 234, and a plurality of pivot pins 236, 238, 240, 242, 244. Link 224 and link 226 are pivotally mounted to, and extend parallel to each other between, upright bracket 216 and load bracket 218. Counterarm 228 is pivotally mounted at a first end 246 to counterarm bracket 230 which is slidably mounted to load bracket 218. Counterarm 228 is pivotally mounted at a second end 248 to first ends 250 of gas cylinders 220 and 222 and is slidably coupled to link 224. The second ends 252 of gas cylinders 222 and 220 are pivotally mounted to upright bracket 216 by pivot pin 242.

Figure 14:
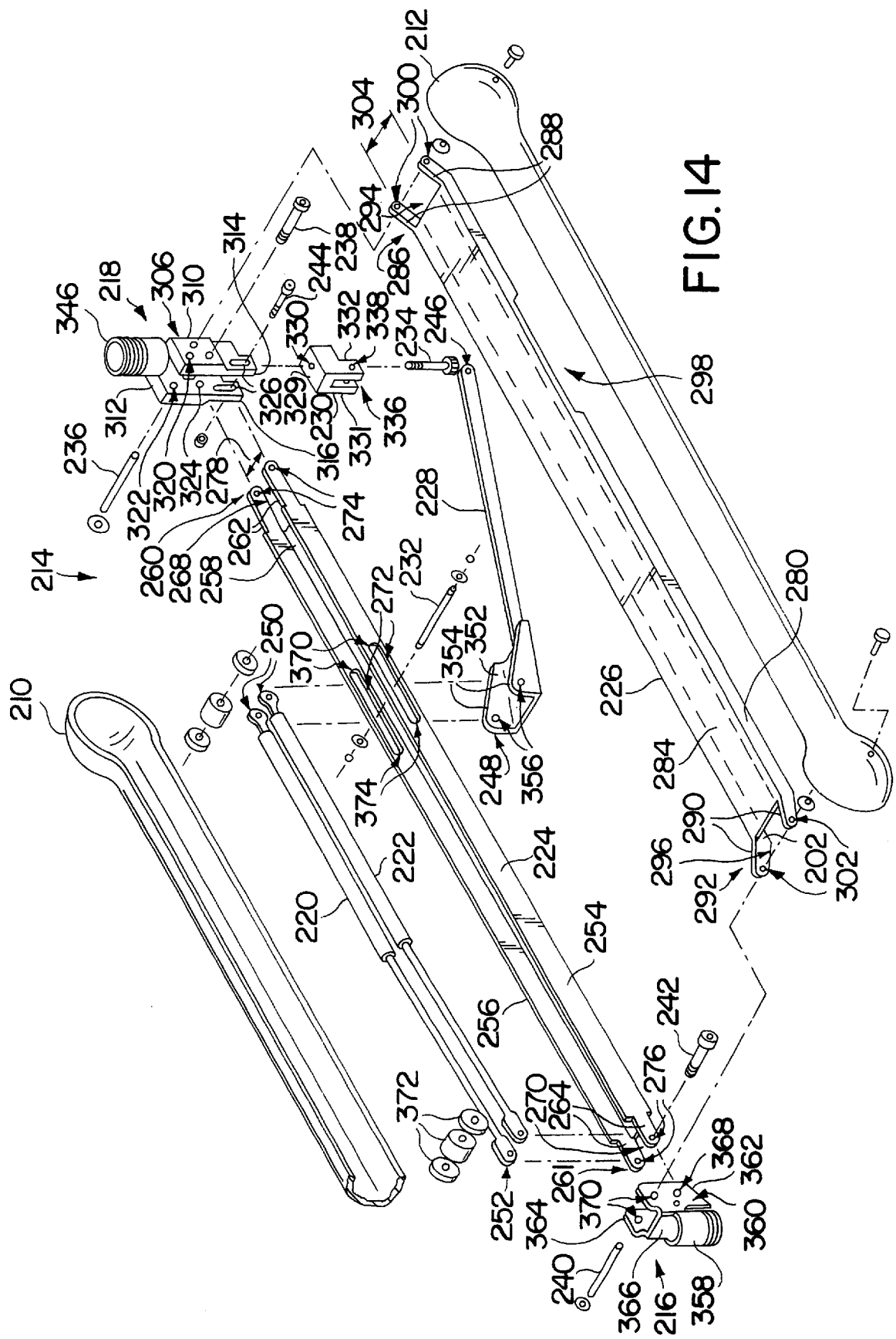
FIG. 14 is an exploded view of a counterbalanced arm in accordance with one aspect of the present invention.
Figure 15:
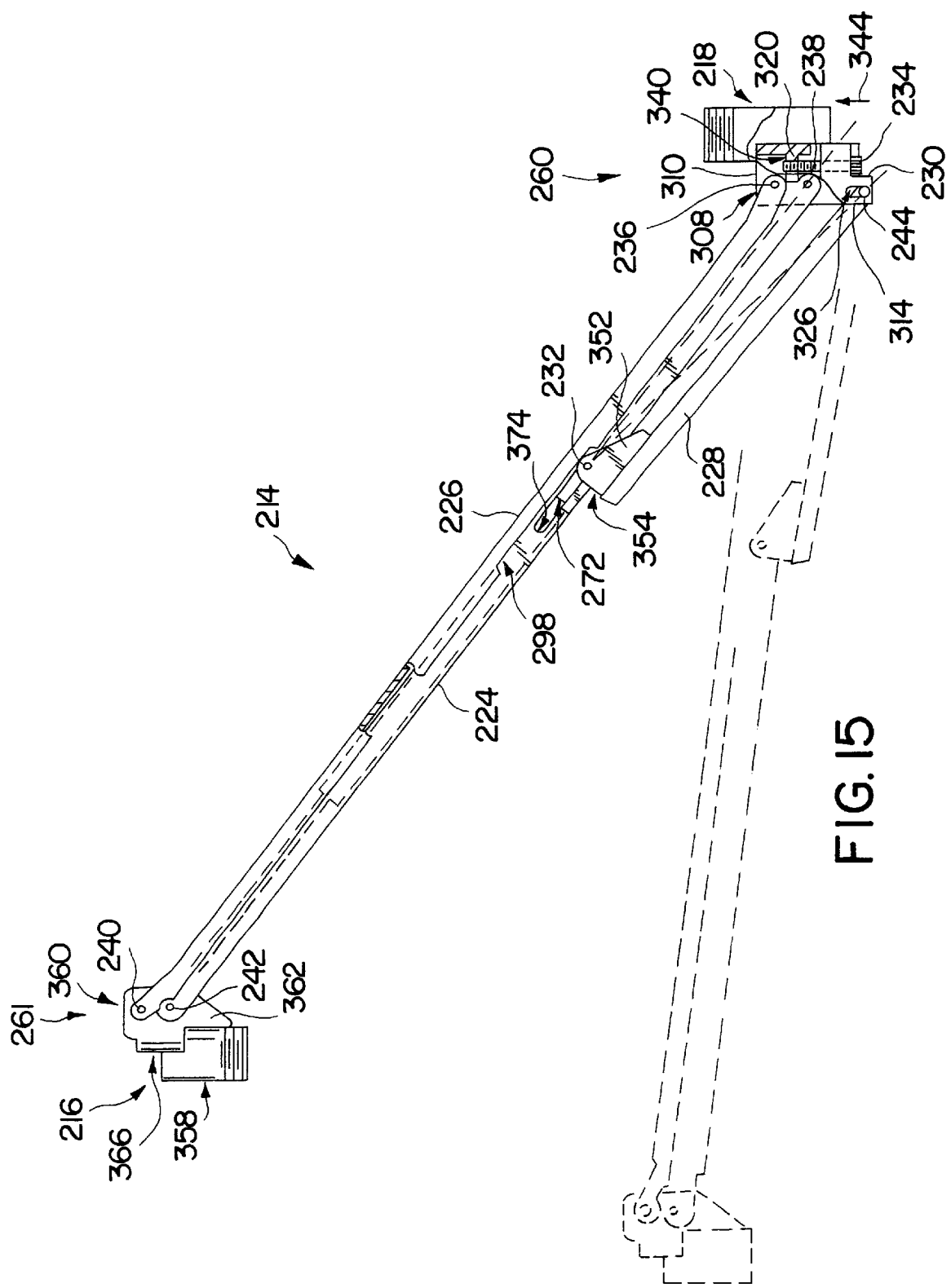
FIG. 15 is a side view of the assembled counterbalanced arm of FIG. 14.

In the illustrated embodiment, bottom link 224 includes two side walls 254 and 256 extending perpendicularly from the bottom wall 258. Bottom link 224 may be constructed in any of several alternative fashions, including, for example, having separate side links corresponding to side walls 254 and 256, or from a hollow rectangular tube which would include a top wall extending between side walls 254 and 256 parallel to bottom wall 258. Bottom link 224 has a width 278. Welded or otherwise mounted to side walls 254 and 256 at a first end 260 of bottom link 224 are mounting ears 262. Mounting ears 264 are also welded or otherwise attached to sidewalls 254 and 256 at second end 261 of bottom link 224. First end 260 and mounting ears 262 define a bottom opening 268 and second end and mounting ears 264 define a bottom opening 270. Side walls 254 and 256, of bottom link 224 are formed to include a slide slot 272 through which slide pin 232 extends to couple counterarm 228 to an intermediate portion of bottom link 224, as shown, for example, in FIGS. 14 and 15.

Mounting ears 262 are formed to include mounting holes 274 through which pivot pin 238 is received to pivotally mount bottom link 224 to upright bracket 218. Mounting ears 264 are formed to include mounting holes 276 through which pivot pin 242 is received to pivotally mount bottom link 224 to load bracket 216. While bottom link 224 has been described as having separate mounting ears 262 and 264 welded or otherwise attached thereto, it is within the teaching of the invention for mounting ears 262 and 264 to be formed integrally with bottom link 224.

Top link 226 includes side walls 280 and 282 and top wall 284. Side walls 280 and 282 extend upwardly from top wall 284. Top link 226 may be constructed in any of several alternative fashions, including, for example, having one or more separate L-shaped links as shown by phantom lines in FIG. 14. Top link 226 has a width 304 which is greater than width 278 of bottom link 224 facilitating assembly of bottom link 224 and top link 226 so that side walls 280 and 282 extend downwardly along the outside of side walls 254 and 256 to form an enclosure. At first end 286, offset mounting ears 288 are welded or otherwise attached to side walls 280 and 282. Likewise, at second end 292, similarly shaped offset mounting ears 290 are welded or otherwise attached to side walls 280 and 282 of top link 226. Offset mounting ears 288 and first end 286 of top wall 284 define a top opening 294 at first end 286. At second end, offset mounting ears 290 and second end 292 of top wall 284 define a top opening 296. Side walls 280 and 282 are formed with the longitudinally extending recess 298 positioned to allow movement of slot pin 232 within longitudinal slide slot 272 when bottom link 224 and top link 226 are positioned adjacent each other.

Offset mounting ear 288 is formed to include mounting holes 300 through which pivot pin 236 passes to pivotally couple first end 286 of top link 226 to upright bracket 218. Likewise, offset mounting ear 290 is formed to include mounting hole 302 through which pivot pin 240 passes to pivotally mount second end 292 of top link 226 to load bracket 216. While top link 226 and offset mounting ears 288 and 290 are described as separate pieces welded or otherwise attached to each other, it is within the teaching of this invention to form top link 226 and offset mounting 288 and 290 as a single integral piece.

Bottom opening 268 and top opening 294 at first ends 260 and 286 of bottom link 224 and top link 226, respectively, facilitate pivoting of arm assembly 214 about upright bracket 218. Bottom opening 270 and top opening 296 at second end 266 and 292 of bottom link 224 and top link 226, respectively, facilitate the pivoting of arm assembly 214 about load bracket 216.

Upright bracket 218 includes a main frame 306 and a mounting shaft 346. Counterbalance adjustment bracket 308 is received in main frame 306. Mainframe 306 includes two upwardly extending ears 310 and 312, two downwardly extending ears 314 and 316, and a cross member 318. Cross member 318 extends between and connects upper ears 310 and 312 and downwardly extending ears 314 and 316. Cross member 318 extends only partially from rear face of main frame 306 towards front face of main frame 306 to avoid interfering with pivoting action of links 224 and 226 and counterarm 228. Upwardly extending ears 310 and 312 are formed to include first mounting holes 322 through which pivot pin 236 passes to couple top link 226 to upright bracket 218. Ears 310 and 312 are also formed to include second mounting holes 324 through which pivot pin 238 passes to pivotally couple bottom link 224 to upright bracket 218. Mounting shaft 346 is welded or otherwise attached to rear of mainframe 306 for coupling counterbalanced arm 66 to other components of the arm assembly 48. Downwardly extending ears 314 and 316 are formed to include adjustment slots 326 through which pivot pin 244 extends to couple counterarm 228 to upright bracket 218.

Counterbalance adjustment bracket 230 includes a top wall 328 and spaced apart ears 332 and 334. Top wall 328 is formed to include an adjustment hole 330. Spaced apart ears 332 and 334 extend downwardly from opposite sides of top wall 328. Top wall 328 and ears 332 and 334 define a channel 336 designed to receive the first end of counterarm 228. Counterbalance adjustment bracket 230 is received between ears 314 and 316 of main frame 306. Ears 332 and 334 are formed to include mounting holes 338 through which pivot pin 244 passes to pivotally mount counterarm 228 to counterbalance adjustment bracket 230 and slidably mount counterbalance adjustment bracket 230 and counterarm 228 to main frame 306.

Cross member 318 is formed to include a threaded hole 340 within which threads of bracket adjustment screw 234 are received. The shaft of counter balance bracket adjustment screw 234 passes through adjustment hole 330 so that tightening of counterbalance bracket adjustment screw 234 will cause counter balance adjustment bracket 230 to move in the direction of arrow 344. When counterbalance bracket adjustment screw 234 is loosened, the weight of the monitor and arm assembly 214 is transferred through counterarm 228 to urge counter balance adjustment bracket 230 downwardly. This movement allows a user to adjust the tension exerted by gas cylinders 220 and 222 at an optimum level to minimize unwanted travel after vertically positioning monitor or camera.

Second end 258 of counterarm 228 is formed to include a yoke 352. Ears 354 of yoke 352 are formed to include mounting holes 356 through which slide pin 232 passes to slidably couple counterarm 228 to bottom link 224 and pivotally mount counterarm 228 to first end 250 of first and second gas cylinders 220 and 222.

Load bracket 216 includes mounting shaft 358 and frame 360. Frame 360 is formed to include ears 362 and 364 and cross member 366. Mounting shaft 358 is welded or otherwise attached to frame 360 and ears 362 and 364. Ears 362 and 364 are formed to include mounting holes 368 through which pivot pin 242 passes to couple second end of bottom link 224 to load bracket 216, and mounting holes 370 through which pivot pin 240 passes to pivotally mount second end of top link 226 to load bracket 216. Second ends 252 of gas cylinders 220 and 222 are pivotally coupled by pivot pin 242 to load bracket 216. Plastic spacers 372 are disposed on pivot pin 242 between ear 364 and second end 252 of gas spring 224, between second end 252 of gas spring 222 and second end 252 of gas spring 220, and between second end 252 of gas spring 220 and ear 364, to maintain alignment of gas springs 220 and 222.

Counterbalanced arm 66 can move between a lower position (shown in phantom lines in FIG. 15) in which slide pin 232 is nearest second end 374 of slot 272 and an upper position (shown in solid lines in FIG. 15) wherein slide pin 232 is nearest first end 376 of slot 272. Gas cylinders 220 and 222 cooperate with friction between mounting ears 262 and 288 and load bracket 218 and mounting ears 264 and 290 and upright bracket 216 to allow counterbalanced arm 66 to be stopped and held in any position between the lower limit and upper limit.

An unillustrated alternative, or additional, device to facilitate elimination of unwanted travel in counterbalanced arm 66, is a brake mechanism similar in construction and operation to the brake mechanisms in main hub 47 and top pivot joint 122. The brake mechanism may be coupled to bottom link 224 and either or both pivot pins 238 and 242. The brake mechanism includes a brake pad in the form of a Rulon® bushing received in a metal cylindrical sleeve through which pivot pins 238 and/or 242 pass, a flange extending inwardly from either of sidewalls 254 and 256 of bottom link 224, and an adjustment screw 384. The inwardly extending flange is formed to include a hole through which the shaft of adjustment screw passes and metal cylindrical sleeve is formed to include a threaded hole in which the threads of shaft of adjustment screw are received. As adjustment screw is tightened and loosened, Brake pad exerts altering frictional forces on pivot pins 242 and 238. This frictional force may be adjusted to eliminate unwanted travel.

Figure 4:
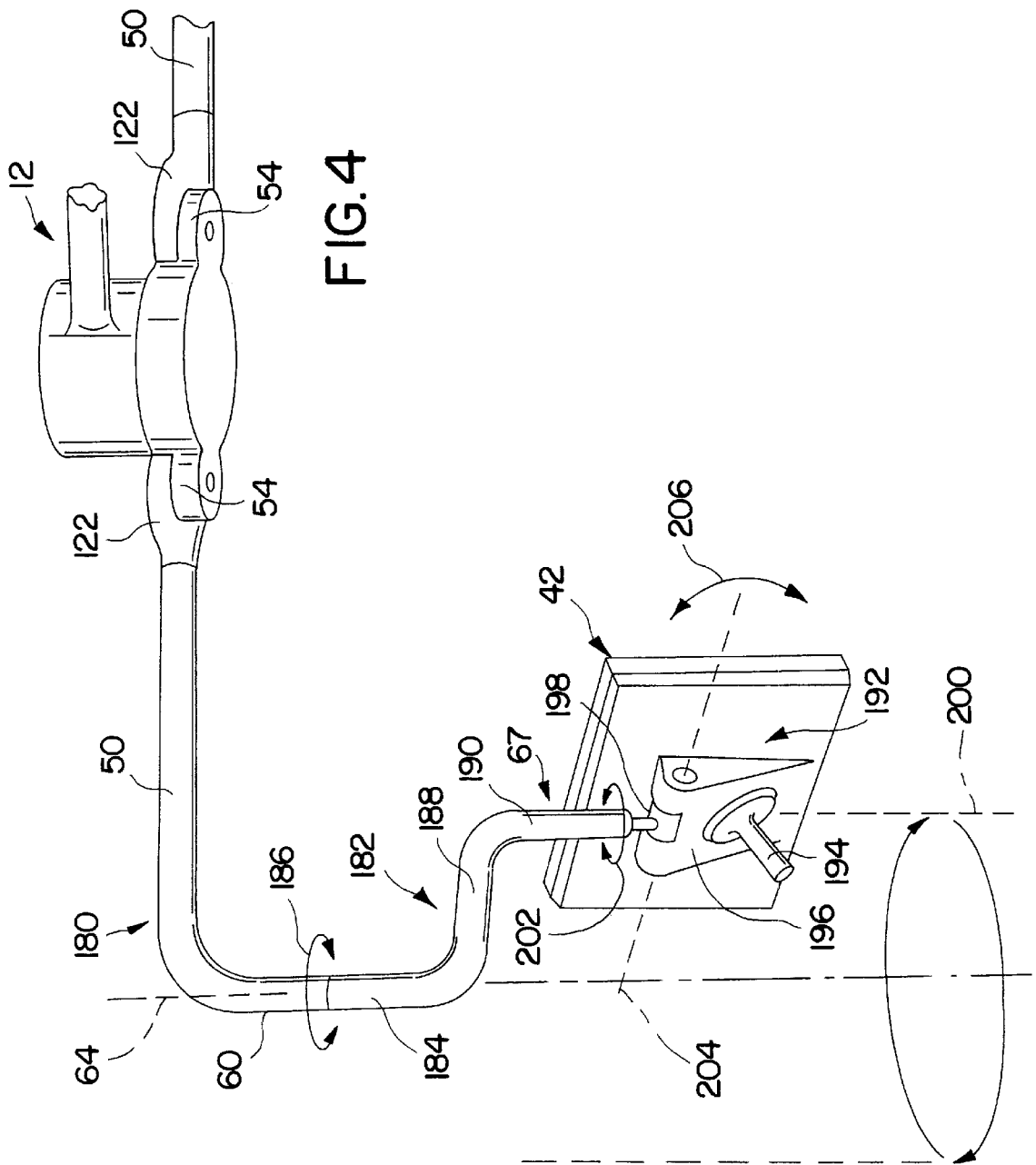
FIG. 4 is a perspective view illustrating a fixed height monitor arm assembly coupled to the central hub of a surgical theater system.

FIG. 4 illustrates a fixed height monitor arm assembly 180. Those elements referenced by the same reference numeral in FIG. 4 as was used to identify a corresponding element in FIG. 1–3 perform the same or similar function as the corresponding element in FIGS. 1–3. Lower vertical arm section 62 and counterbalanced arm 66 are replaced by an offset or S-shaped section 182 including an upper section 184 rotatably coupled to arm section 60 about axis 64 as illustrated by double-headed arrow 186. A central, horizontal arm section 188 extends between upper arm section 184 and a lower arm section 190. A mounting assembly 192 couples the arm portion 182 to the monitor 42. A handle 194 is coupled to a monitor support 196. A shaft 198 is rotatably coupled to arm section 190 about axis 200 as illustrated by double-headed arrow 202. Arm 198 is also coupled to support 196 for pivotable movement about axis 204 as illustrated by double-headed arrow 206.

Many health care facilities include multiple OR suites in which the healthcare staff may wish to perform operations to be filmed or in which video images may be useful in facilitating the surgical operation. Often less than all of the OR suites will be utilized at the same time. Even if all OR suites are in use at the same time, often not all of the operations being simultaneously performed will need to be filmed or will require monitors providing images for the surgeon. Occasionally, surgical procedures will be performed that will require two cameras and only a single monitor or three monitors and no camera. Therefore, in accordance with another aspect of the present invention, a surgical theater system 10 includes either a multipurpose arm 648 configured to removably receive a camera 108, and/or a monitor 42 and 44 or a multi-purpose receptacle 745 configured to receive a camera arm 790 or a monitor arm 748. As shown for example, in FIGS. 16 and 17, embodiments of the surgical theater system 10 are provided to facilitate reconfiguration of the surgical theater system 10 by adding or removing cameras 108 or monitors 42 and 44 from the assembly. In one of these embodiments, a multi-purpose arm 648 is provided configured to support either a monitor mount 649 or a camera mount 647. In a second embodiment, a multi-purpose receptacle 745 is provided configured to support either a monitor arm 748 or a camera arm 790. The multi-purpose arm 648 and the multi-purpose receptacle 745 each include a mechanical connector for mechanically coupling either a monitor mount 649 or a monitor arm 748 or a camera mount 647 or a camera arm 790 to the multi-purpose arm 648 or multipurpose receptacle 745. Each multi-purpose arm 648 and multi-purpose receptacle 745 also includes one or more standard video couplings located adjacent the mechanical connector for attachment to the video lead coupled to a camera 108 and/or a monitor 42 and 44.

Thus, a health care facility upon installation of a surgical theater system in accordance with the present invention is capable of reconfiguring the surgical theater system to provide as many monitors 42 and 44, and cameras 108, or combinations of monitors 42 and 44, and cameras 108 as the apparatus has multipurpose arms 648 or multi-purpose receptacles 745. It is within the teaching of the disclosure for multi-purpose arms 648 and multi-purpose receptacles 745 to be configured to receive other device mounts and arms, such as, for example, surgical lighthead mounts and arms, respectively.

Figure 17:
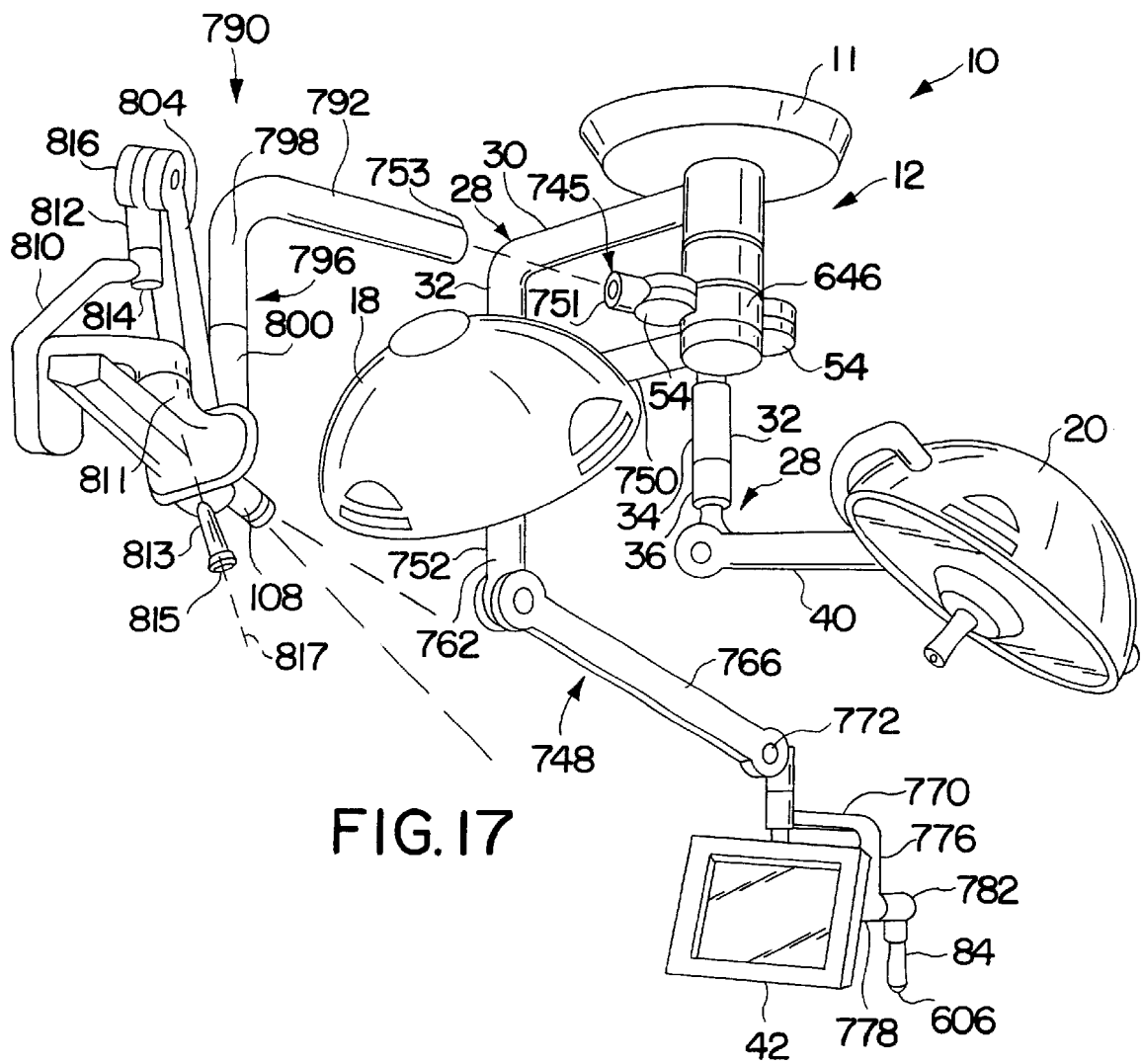
FIG. 17 is a perspective view of a surgical theater system having two lights mounted by light arm assemblies for rotation about a hub, and two multipurpose receptacles mounted for pivotal movement about pivot joints mounted for rotation about the hub, one of the multi-purpose receptacles includes a monitor arm mounted to its distal end, while the other multi-purpose receptacle has a camera arm disconnected from its distal end.

FIGS. 16 and 17 illustrate two alternative embodiments of such a surgical theater system 10, however, additional non-illustrated embodiments providing a single or a plurality of multi-purpose arms or receptacles or multi-purpose arms or receptacles providing for disconnection at different locations are within the scope of the invention as presently perceived. It is within the scope of the invention to provide a plurality of similarly configured surgical theater systems 10 throughout a healthcare facility between which monitors 42 and 44 and/or cameras 108 may be exchanged.

FIG. 16 illustrates a first configurable surgical light apparatus having a pair of surgical light heads 18, 20 coupled to a central hub 12, and a pair of multipurpose arms 648 coupled to pivot joints 54 on hub 12. Surgical light support arms include horizontally extending sections 30 and vertically extending sections 32. Vertically extending arm sections 32 include upper and lower sections 34 and 36 so that the vertical sections 32 are rotatable about an axis 38 (shown in FIG. 1). A counterbalanced arm 40 is pivotally coupled to vertical arm section 32 for supporting surgical lights 18 and 20.

Figure 18:
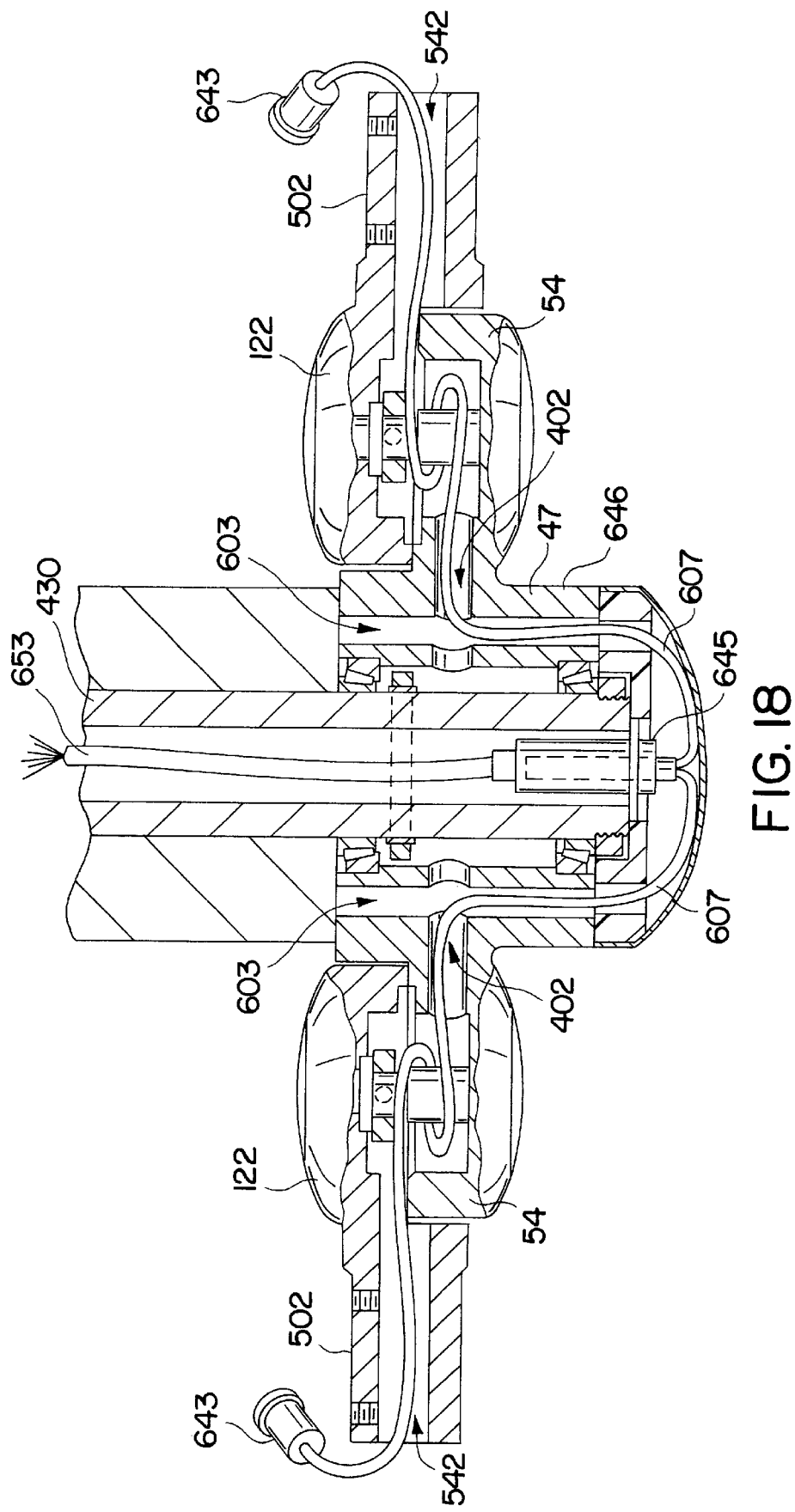
FIG. 18 is a sectional view of a portion of the central hub of the surgical theater system of FIG. 17 showing an upper dedicated hub to which a device, such as a surgical light, is attached and a lower multi-purpose hub, similar to the hub of FIGS. 5 and 6, configured so that each upper pivot joint acts as a multi-purpose receptacle having an electrical connector extending therefrom.

Monitors 42 and 44 and/or camera are coupled to multi-purpose hub 646 by multi-purpose arm assemblies 648. Multi-purpose hub 646 is similar to connection hub 46 and identical or similar reference numerals will be used to identify identical and similar components. It is to be understood that the description of connection hub 46 set forth above is generally applicable to multi-purpose hub 646. While multi-purpose hub 646, illustrated in cross-section in FIG. 18, is illustrated as being used only with multi-purpose arm assembly 648 and multi-purpose receptacle 745, multi-purpose hub 646 is adaptable for use with any of the illustrated surgical theater systems. Similarly, connection hub 46 is adaptable for use with any of the illustrated surgical theater system embodiments.

Multi-purpose hub 646 includes a slip ring assembly 645 configured for attachment to the lower end of shaft. Cable 653 extends internally through shaft 430 and is electrically coupled to a first end of slip ring assembly 645. Illustratively, cable 653 includes twenty-eight wires which carry power, ground and video signals to or from two separate video devices. Two cables 607 are electrically coupled to second end of slip ring assembly 640. Each cable 607 includes fourteen wires which carry power, ground and video signals to or from a single video devices. Slip ring assembly 645 includes 28 sets of slip rings to transfer the power, ground and video signals between the wires of cable 653 and cable 607. Illustratively, slip ring assembly 645 is commercially available from AirFlite, as part number # 100164-001.

Multi-purpose hub 646 includes a pair of diametrically opposed longitudinally extending holes 603 cast or machined in the main hub section 47. Each longitudinal hole 603 intersects with a respective radially extending hole 402 to permit passage of cables 603 extending from second end of slip ring assembly 645 into lower pivot joint 54 and out of distal end of wire bore 542 of arm connection section 502 of top pivot joint 122. Each cable 607 terminates in an electrical connector 643 configured for attachment to an arm cable coupled to a video device.

Each multi-purpose arm 648 is identical to the other and is very similar to monitor support arm assembly 48. Thus, except where otherwise noted below, the description of monitor support arm assembly 48 above accurately describes multipurpose arm 648 and will not be repeated. Components in multi-purpose arm 648 that are similar to corresponding components in monitor support arm assembly 48 will be identified with similar reference numerals.

Illustratively, a multi-purpose arm assembly 648 includes a bent arm or first segment having a horizontal arm section 650 and a vertical arm section 652. Horizontal arm sections 650 are coupled to bottom pivot joints 54 which extend away from a main hub section 47 of connection hub 646. Therefore, the horizontal arm sections 650 are pivotable about pivot axes 56 and 58 (shown in FIG. 1) which are spaced apart from the pivot axis 26 (shown in FIG. 1) of central hub 12.

Vertical arm sections 652 of multi-purpose arm assemblies 648 illustratively include first and second sections 660 and 662. The second vertical section or extension arm 662 is rotatable relative to the first vertical section 660 about axis 64 (Shown in FIG. 1). Counterbalanced arms 666 are pivotally connected to second vertical section 662 by a pivot connection 668 located at the proximate end of counterbalanced arm 666. A second pivot connection 672 is located at the distal end of counterbalanced arm 666.

Multi-purpose arms 648 include a coupling 651 coupled to pivot connection 672 at the distal end of a counterbalanced arm section 666 of the multipurpose arm 648. A monitor 42 is shown mounted to the first multi-purpose arm 648 via a monitor mount 649. A camera coupled to a camera mount 647 and a second monitor 44 coupled to a monitor mount 649 are shown disconnected from the second multi-purpose arm 648. Camera mount 647 and both monitor mounts 649 are each provided with one half of a mechanical quick disconnect coupling 655 of a known type configured to connect to a second half of a mechanical quick disconnect coupling 651 mounted to pivot connection 672 on the distal end of counterbalanced arm section 666 of multi-purpose arm 648.

Monitor mount 649 includes a horizontal arm 670 coupled to hub 674. Hub 674 is coupled to first half of connector 653. A vertical arm 676 is coupled to horizontal arm section 670. A monitor mounting arm 678 has a first end rotatably coupled to a hub 682 of vertical arm 676. A handle 84 is coupled to the first end of monitor mounting arm 678. Illustratively duplicate toggle switch 606 is mounted to handle 84. A second end of mounting arm 678 is coupled to a monitor support plate (not shown) mounted to monitor 42 and 44. The description of the movement of monitor mounting arm assembly 48 set forth above accurately describes the movement of multi-purpose arm 648 when monitor mount 649 is coupled thereto and will not be repeated. Cables (not shown) run through monitor mount 649 to provide power and video signals to monitor 42 and 44. These cables terminate in an electrical connector (not shown) located adjacent to mechanical coupling 653 for coupling cables of monitor mount 649 to a connector (not shown) located adjacent mechanical coupling 651 of multi-purpose arm 648. Electrical connectors facilitating the coupling of video equipment are well known in the art and are therefore not described.

Camera mount 647 includes a first half of a quick disconnect coupling 655 coupled to hub 714. Camera mount 647 includes a camera mounting arm 710 rotatably mounted to coupling 653 by hub 714. A pan/tilt mechanism housing 711 is coupled to mounting arm 710 and camera 108. Housed in housing 711 are motors and mechanisms permitting remote panning and tilting of camera 108. Camera 108 includes internal mechanisms, motors and controls to facilitate focus adjustment, zooming, iris adjustment, and white balance adjustment. Extending downwardly from camera hub 711 is handle 713 including on/off switch 715 electrically coupled to turn camera 108 on and off. In one preferred embodiment, handle 713 includes a longitudinal axis 717. Handle 713 is mounted to camera hub 711 for pivotal movement about the longitudinal axis 717. Pivotal movement of handle 713 about longitudinal axis 717 actuates an actuator coupled to the zoom mechanism of the camera 108.

Preferably, handle 713 also includes an actuator (not shown) such as a button to adjust the focus of the camera 108. It is within the teaching of the present invention for handle 713 to be a sterile handle so that a surgeon or other operating room personnel can turn the camera on and off during an operation. It is understood that any suitable camera 108 may be used.

Cables (not shown) run through camera mount 647 to provide power, pan, zoom, tilt, focus, white balance, and iris signals to, and video signals from camera 108. These cables terminate in an electrical connector (not shown) located adjacent to mechanical coupling 653 for coupling cables of camera mount 647 to a connector (not shown) located adjacent mechanical coupling 651 of multi-purpose arm 648.

Multi-purpose arm 648 is provided with radial holes to permit passage of cables containing thirty-two wires (not shown). Twenty of these thirty-two wires provide power, pan, zoom, tilt, focus, white balance, and iris signals to, and video signals from camera 108, when camera mount 647 is attached to multi-purpose arm 648. It should be understood that all cameras 108 attached to multi-purpose arm will not have mounts and mechanisms facilitating remote control of panning, zooming, tilting, white balancing, and iris adjustment. The remaining 12 wires provide power and video signals to a monitor 42 and 44 when a monitor 42 and 44 is attached to multi-purpose arm 648.

It should be understood that multi-purpose arm 648 may be provided with standard brake mechanisms within counterbalanced arm section 666 to lock counterbalanced arm 666 at a location prior to removal of camera mount 647 or monitor mount 649 and replacement with another camera mount 647 or monitor mount 649. Alternatively, quick disconnect coupling 651 may be provided with mechanisms prohibiting removal of a camera mount 647 or monitor mount 649 unless counterbalanced arm 666 is placed in its uppermost raised location as shown in FIG. 16. Other mechanisms and methods of attachment and detachment of mounts 647 and 649 which inhibit a rapid movement of counterbalanced arm 666 to its uppermost raised location upon removal of a camera mount 647 or monitor mount 649 are within the scope of the invention as presently perceived.

It should be understood that monitor mount 649 and camera mount 647 may include ballast so that the weight of camera mount 647 and monitor mount 649 can be adjusted to a selected weight for which the counterbalanced arm 666 is calibrated. It is also within the teaching of this invention as presently perceived to provide counterbalanced arm 666 with calibration mechanisms to adjust counterbalanced arm 666 for proper operation when coupled to loads of different weights.

FIG. 17 illustrates a second configurable surgical theater system 10 having a pair of surgical light heads 18, 20 coupled to a central hub 12, and a pair of multi-purpose receptacles 745 (only one of which is visible in FIG. 17) configured to be coupled at one end to a monitor arm 748 or a camera arm 790 and at the other end to a pivot joint 54 on hub 12. Surgical light support arms 28 include horizontally extending sections 30 and vertically extending sections 32. Vertically extending arm sections 32 include upper and lower sections 34 and 36 so that the vertical sections 32 are rotatable about an axis 38 (shown in FIG. 1). A counterbalanced arm 40 is pivotally coupled to vertical arm section 32 for supporting surgical lights 18 and 20.

Monitor 42 and/or camera 108 are coupled to multi-purpose hub 646 by a dedicated monitor arm 748 or a dedicated camera arm 790 respectively coupled to multi-purpose receptacle 745. Each multi-purpose receptacle 745 is substantially identical to the other. Multi-purpose receptacles 745 include a coupling 751 at their distal ends and are coupled at their proximate ends for pivotal movement about pivot joint 54.

A monitor 42 is shown mounted to the first multi-purpose receptacle 745 via a monitor arm 748 and a camera 108 coupled to a camera arm 790 is shown disconnected from the second multi-purpose receptacle 745. It should be understood that a second monitor arm 748 could be coupled to second multi-purpose receptacle 745 to provide a surgical theater system with two monitors. Similarly, a second camera arm could be coupled to the first multi-purpose receptacle to provide a surgical theater system with two cameras. Camera arm 790 and monitor arm 748 are each provided with one half of a mechanical coupling 753 configured to connect to a second half of a mechanical coupling 751 mounted to multi-purpose receptacle 745. In the illustrated embodiment, the proximate end of monitor arm 648 and camera arm 790 slide over the arm connection section 502 of top pivot joint 122 and are bolted thereto to provide mechanical connection. It will be understood that it is within the teaching of the disclosure to provide arm connection section 502 of top pivot joint 122 with one half a standard mechanical quick disconnect connection and to provide the proximate ends of monitor arm 748 and camera arm 790 with the other half of a standard mechanical quick disconnect section.

Monitor arm 748 is very similar to monitor support arm assembly 48. Thus, except where otherwise noted below, the description of monitor support arm assembly 48 above accurately describes monitor arm 748 and will not be repeated. Components in monitor arm 748 that are similar to corresponding components in monitor support arm assembly 48 will be identified with similar reference numerals.

Figure 19:
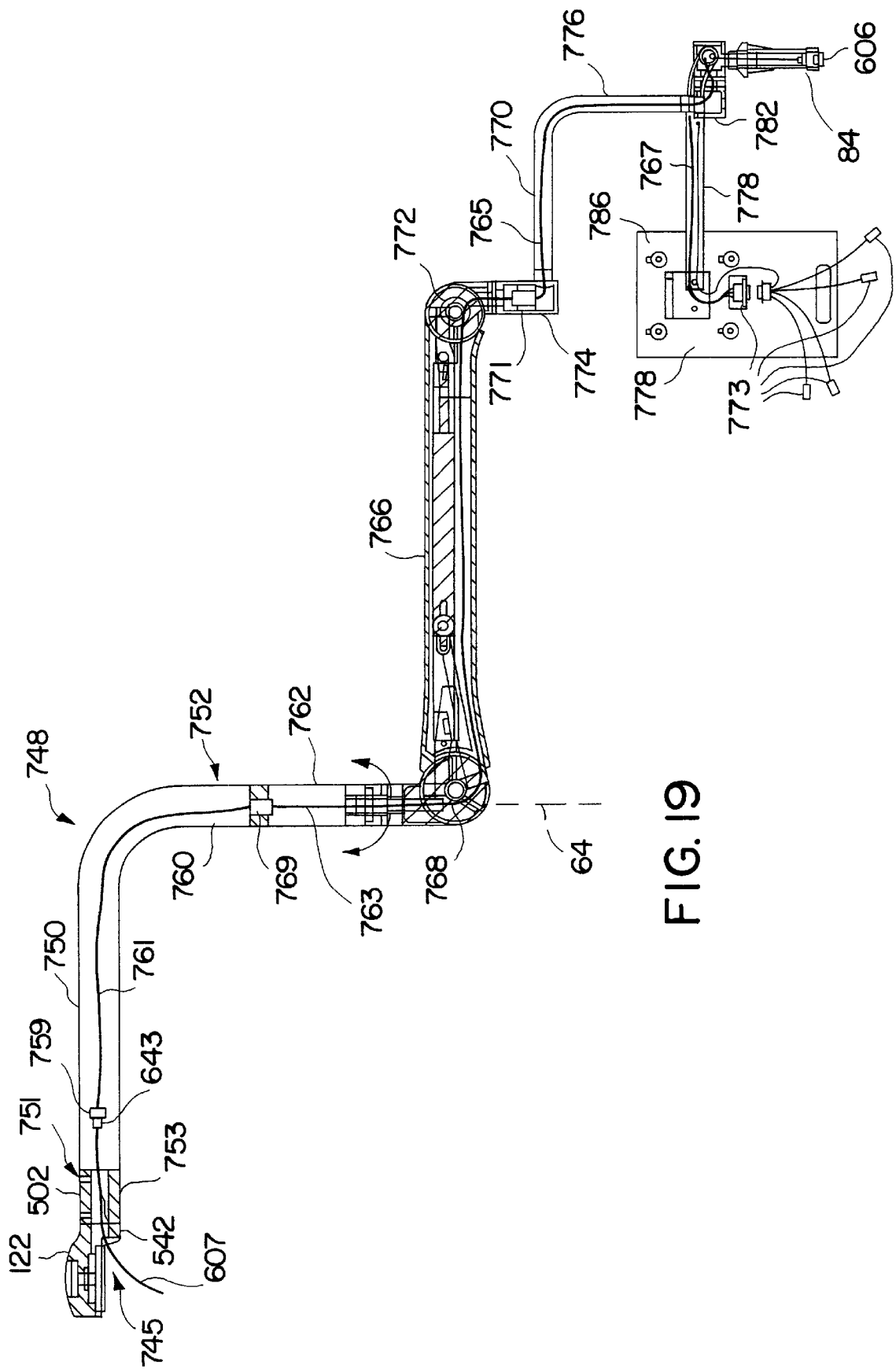
FIG. 19 is a side view with parts broken away of a monitor arm for attachment to the multi-purpose receptacles of FIG. 18.
Figure 20:
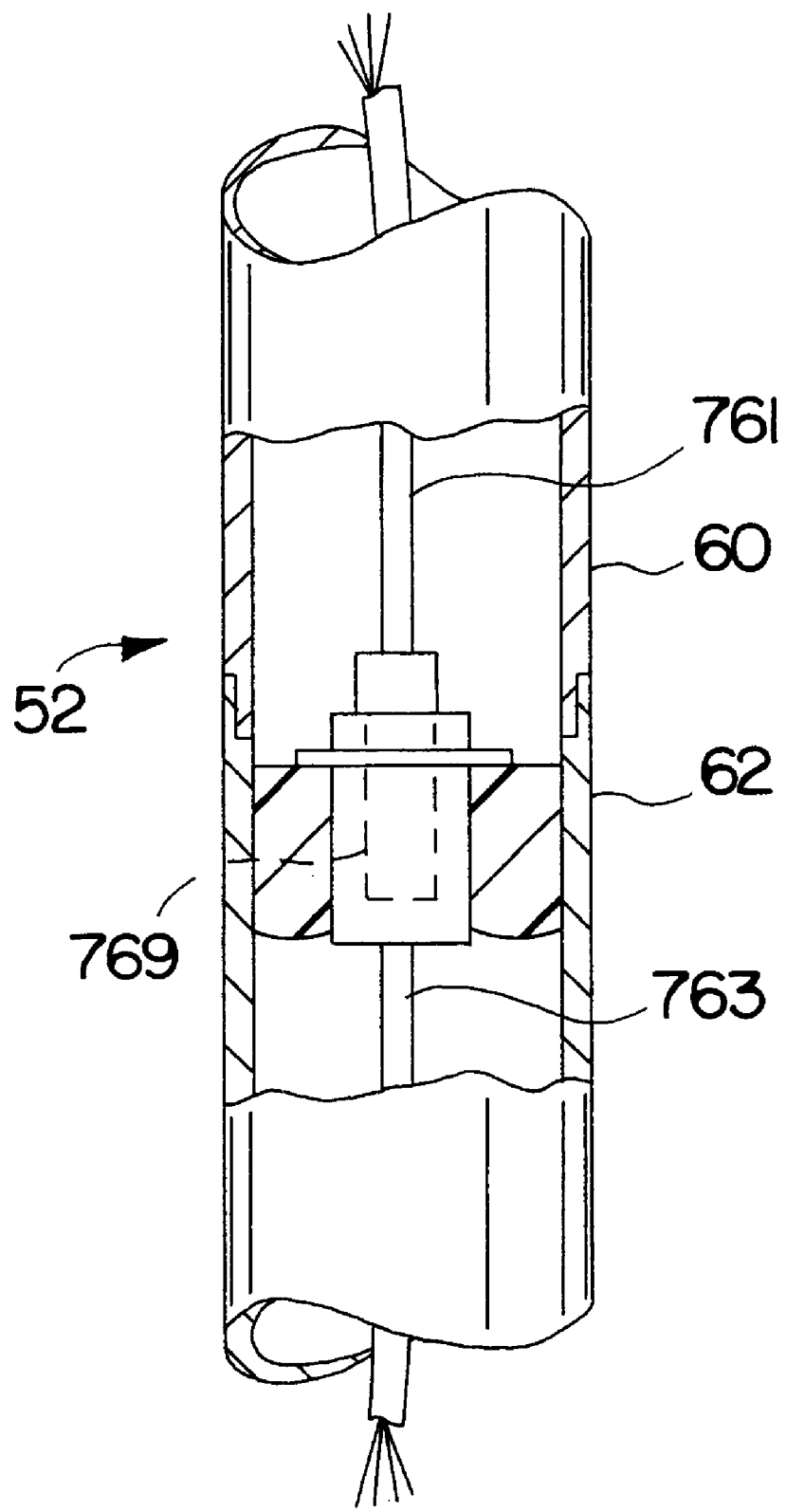
FIG. 20 is an auxiliary view of the portion of the monitor arm of FIG. 19 enclosed in circle 20—20.
Figure 21:
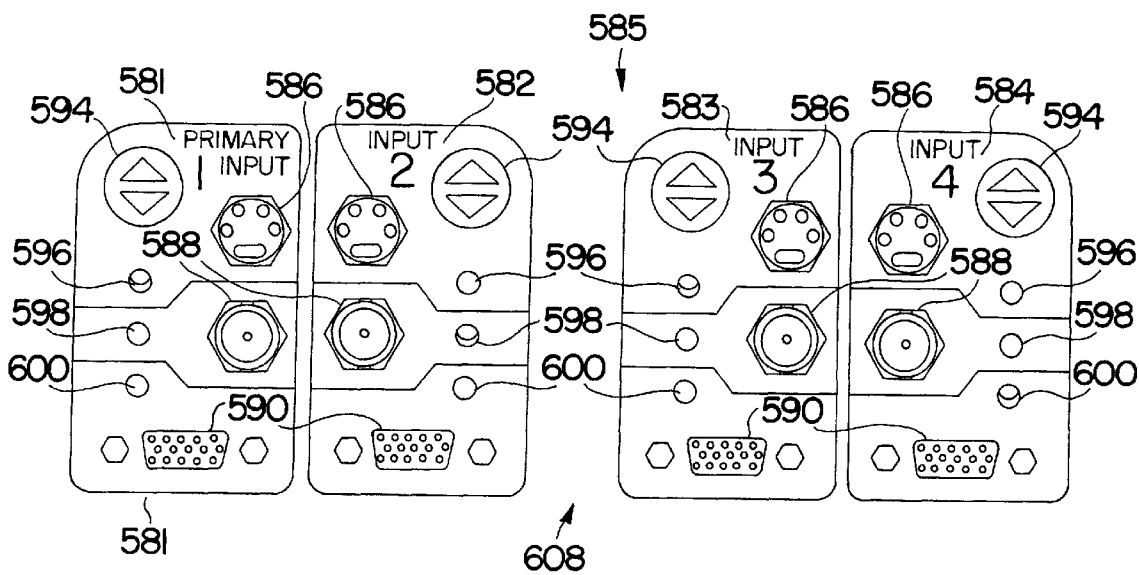
FIG. 21 is a plan view of a remotely mounted input controller of a selector control panel electrically coupled to the monitors of the surgical theater system showing controls for four input channels each of which includes three connectors to which video devices may be coupled to provide a video image to the monitors of the surgical theater system or another monitor coupled to a remote output, each input channel controller is provided with a selector switch by which an active connector is selected and indicator lights configured to display which of the three connectors is active.
Figure 22:
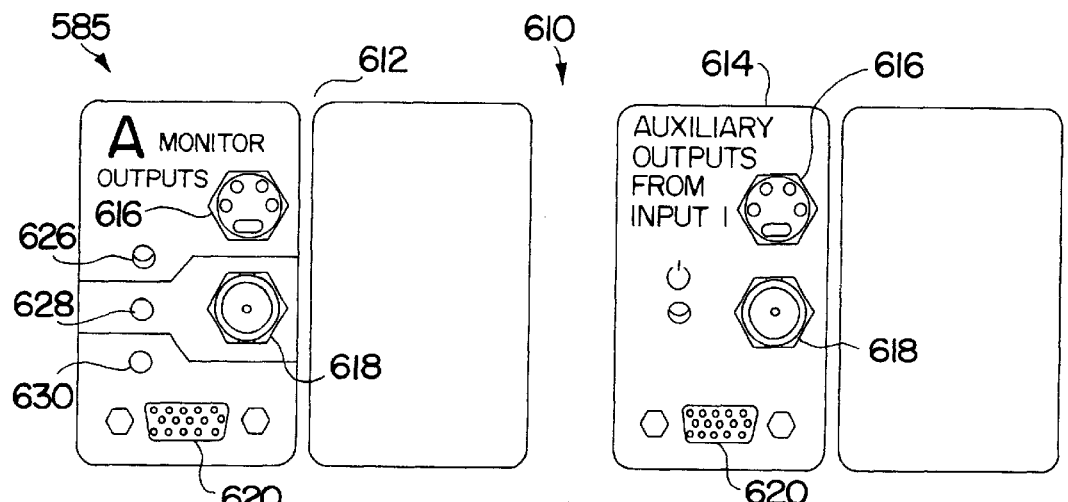
FIG. 22 is a plan view of a remotely mounted output panel of a selector control panel showing an "A" monitor output sub-panel electrically coupled to the video feed of the primary or "A" monitor of the surgical theater system and an Auxiliary output sub-panel directly coupled to the primary inputs of channel 1 of the input controller each output sub-panel includes three connectors to permit monitors or other video display devices to be coupled thereto.

Referring to FIGS. 17, 19, and 20, a monitor arm 748 is illustrated. Illustratively, monitor arm 748 includes a bent arm or first segment having a horizontal arm section 750 and a vertical arm section 752. Horizontal arm section 750 includes a first half of a mechanical coupling at its proximate end configured for coupling to a second half of a coupling 751 at distal end of multi-purpose receptacle 745. As mentioned above, multi-purpose receptacle 745 is coupled at its proximate end to bottom pivot joints 54 which extend away from a main hub section 47 of connection hub 46. Therefore, the horizontal arm sections 750 are pivotable about pivot axes 56 and 58 (shown in FIG. 1) which are spaced apart from the pivot axis 26 (shown in FIG. 1) of central hub 12.

Vertical arm sections 752 of monitor arm 748 illustratively includes first and second sections 760 and 762. The second vertical section or extension arm 762 is rotatable relative to the first vertical section 760 about axis 64. Counterbalanced arms 766 are pivotally connected to second vertical section 762 by a pivot connection 768 located at the proximate end of counterbalanced arm 766. A second pivot connection 772 is located at the distal end of counterbalanced arm 766.

A horizontal arm 770 coupled by hub 774 to second pivot connection 772 of counterbalanced arm 766. A vertical arm 776 is coupled to horizontal arm section 770. A monitor mounting arm 778 has a first end rotatably coupled to a hub 782 of vertical arm 776. A handle 84 is coupled to the first end of monitor mounting arm 778. Illustratively duplicate toggle switch 606 is mounted to handle 84. A second end of mounting arm 778 is coupled to a monitor support plate 786 mounted to monitor 42.

The description of the movement of monitor mounting arm assembly 48 set forth above accurately describes the movement of monitor arm 748 and multipurpose receptacle 745 when monitor arm 748 is coupled thereto and will not be repeated. Cables run through monitor arm 748 to provide power and video signals to monitor 42, which illustratively include cable 761, cable 763, cable 765, cable 767. Illustratively, cable 761 terminates in an electrical connector 759 located adjacent to mechanical coupling 753 for coupling to connector 643 of cable 607 located adjacent mechanical coupling 751 of multi-purpose receptacle 745. The other end of cable 761 is coupled to a first end of slip ring assembly 769 mounted frictionally mounted in lower arm 62 of vertical arm 52 adjacent to the point where lower arm is rotatably coupled to upper arm. Illustratively, slip ring assemblies 769 and 771 are available from Litton Systems, Inc., Blacksburg, Va., as part number AC6319. Such slip ring assemblies include 14 sets of slip rings allowing two power and twelve signals to be transferred between cables on opposite sides of rotating components.

The second end of slip ring assembly 769 is coupled to a first end of cable 763 which runs through lower arm 762 and counter balanced arm 766. Second end of cable763 is coupled to a first end of slip ring assembly 771. Slip ring assembly 771 is frictionally mounted within hub774 adjacent to the point where hub 774 is rotatably mounted to second pivot connection 772 of counterbalanced arm 766. Second end of slip ring assembly 771 is electrically coupled to first end of cable 765 which extends through hub 774, horizontal arm 770, vertical arm 776 and hub 772. The other end of cable 765 is coupled through switch 606 to one end of cable 767. Cable 767 extends through monitor mounting arm 778 and terminates in a plurality of connectors 773 for coupling to a monitor.

Camera arm 790 is similar to camera mounting arm assembly 90 so similar reference numerals will be used for similar components. The major differences between camera arm 790 and camera arm mounting assembly 90 are the cables running through the camera arm 790 and camera mounting arm assembly 90 and the fact that the camera arm 790 includes couplings for mounting to multi-purpose receptacle 745 rather than being mounted to a separate camera hub 94 like camera mounting arm assembly 90. Camera arm 790 also includes a mechanism housing 811 in which remotely operable pan/tilt motors and mechanisms are housed.

Camera arm 790 includes a horizontal arm section 792 having a proximate end including a first half of a mechanical coupling 753 configured to mate with second half of mechanical coupling 751 of multi-purpose receptacle 745 mounted to pivot joint 54 of hub 646 of central hub 12. A vertical arm section 796 is coupled to distal end of horizontal arm section 792. Vertical section 796 includes a first, upper section 798 and a second, lower arm section 800 rotatably coupled to arm section 798 about axis 102 (shown in FIG. 1). A counterbalanced arm 804 is coupled to lower vertical section 800 by a pivot connection (not shown). Shaft 812 is pivotally connected to counterbalanced arm 804 by pivot connection 816.

Camera mounting arm 810 is rotatably mounted on shaft 812 by hub 814. A pan/tilt mechanism housing 811 is coupled to mounting arm 810 and camera 108. Housed in housing 811 are motors and mechanisms permitting remote panning and tilting of camera 108. Camera 108 includes internal mechanisms, motors and controls to facilitate focus adjustment, zooming, iris adjustment, and white balance adjustment. Extending downwardly from camera housing 811 is handle 813 including on/off switch 815 electrically coupled to turn camera 108 on and off. In one preferred embodiment, handle 813 includes a longitudinal axis 817. Handle 813 is mounted to camera hub 811 for pivotal movement about the longitudinal axis 817. Pivotal movement of handle 813 about longitudinal axis 817 actuates an actuator (not shown) coupled to the zoom mechanism of the camera 108. Preferably, handle 813 also includes an actuator (not shown) such as a button to adjust the focus of the camera 108. It is within the teaching of the present invention for handle 813 to be a sterile handle so that a surgeon or other operating room personnel can turn the camera on and off during an operation. It is understood that any suitable camera 108 may be used.

Cables (not shown) run through camera arm 790 to provide power, pan, zoom, tilt, focus, white balance, and iris signals to, and video signals from camera 108. These cables terminate in an electrical connector (not shown) located adjacent to mechanical coupling 753 for coupling cables of camera arm 790 to a connector (not shown) located adjacent mechanical coupling 751 of multi-purpose receptacle 745. Slip rings of the type described with regard to monitor arm 748 facilitate rotation of components of camera arm 790 relative to each other.

Multi-purpose receptacle 745 is provided with radial holes to permit passage of cables therethrough for coupling to cables within camera arm. When the camera 108 and camera mount 811 may be remotely controlled, such cable contains fourteen wires (not shown). These wires provide power, pan, zoom, tilt, focus, white balance, and iris signals to, and video signals from camera 108, when camera arm 790 is attached to multi-purpose receptacle 745 and an indicator signal to indicate whether the cable is carrying signals for a monitor or camera. It should be understood that all cameras 108 attached to camera arms will not have mounts and mechanisms facilitating remote control of panning, zooming, tilting, white balancing, and iris adjustment.

Referring to FIGS. 21–26, two embodiments of controls for a surgical theater system are shown. As will be explained in detail hereafter, a surgical theater system is provided with a video monitor mounted to an arm extending from the hub of the surgical theater system. The monitor is adapted to display images received from a plurality of video inputs coupled to a plurality of video devices. A controller is coupled between the plurality of video inputs and the monitor to control the image that is displayed on the monitor. The controller may include switches mounted away from, but coupled to, the surgical theater system hub and switches mounted to the monitor arm or the monitor for selecting the video input providing the image displayed by the monitor.

Controls facilitate selectively displaying images from a plurality of video devices 592. Each of the embodiments includes a selector control panel 585 and 636 having an input control panel 608 and 638 and an output panel 610. Each input control panel 608 and 638 includes a plurality of connectors 586, 588, 590 configured for coupling to a plurality of video devices 592 providing a video feed, selector buttons 594, 640, 642 for selecting which connector 586, 588, 590 is active, and indicator lights 596, 598, 600 indicating the active connector. Each output panel 610 includes a plurality of connectors 616, 618, 620 configured to be coupled to a monitor or video display device located remotely from the surgical theater system (not shown). Each embodiment allows a video feed from a camera 108 mounted to the surgical theater system 10 or a remote video device to be displayed on the monitors 42 and 44 of the surgical theater system or on remote monitors or video displays coupled to the output panel 610.

In the preferred embodiment, shown, for example, in FIGS. 21–24, a remotely mounted selector control panel 585 includes a multi-channel input panel 608, an output panel 610, and monitor input selector panel 595. The multi-channel input panel 608 is coupled to one or two monitors 42 and 44 coupled to the hub of the surgical theater system. In the illustrated embodiment, four channels 581–584 are provided through which video signals from a plurality of video devices 592 are transmitted.

As shown for example in FIGS. 21–24, selector device 580 includes a selector control panel 585, a power supply 622, and a switcher 632. Selector control panel 585 includes a multi-channel input selector panel 608 having four channels, referred to hereinafter as channels 1–4 (581, 582, 583, 584 respectively). Each channel 581–584 includes three different types of video connectors, i.e. a y-c connector 586 (shown as squares in FIG. 24), a composite connector 588 (shown as triangles in FIG. 24), and an RGB connector 590 (shown as circles in FIG. 24), to facilitate coupling a wide variety of video input devices 592 to each channel 581–584. Each channel 581–584 includes a selector switch 594 permitting the user to select between available connectors 586, 588, 590 to designate an active connector providing the video feed for that channel.

Figure 24:
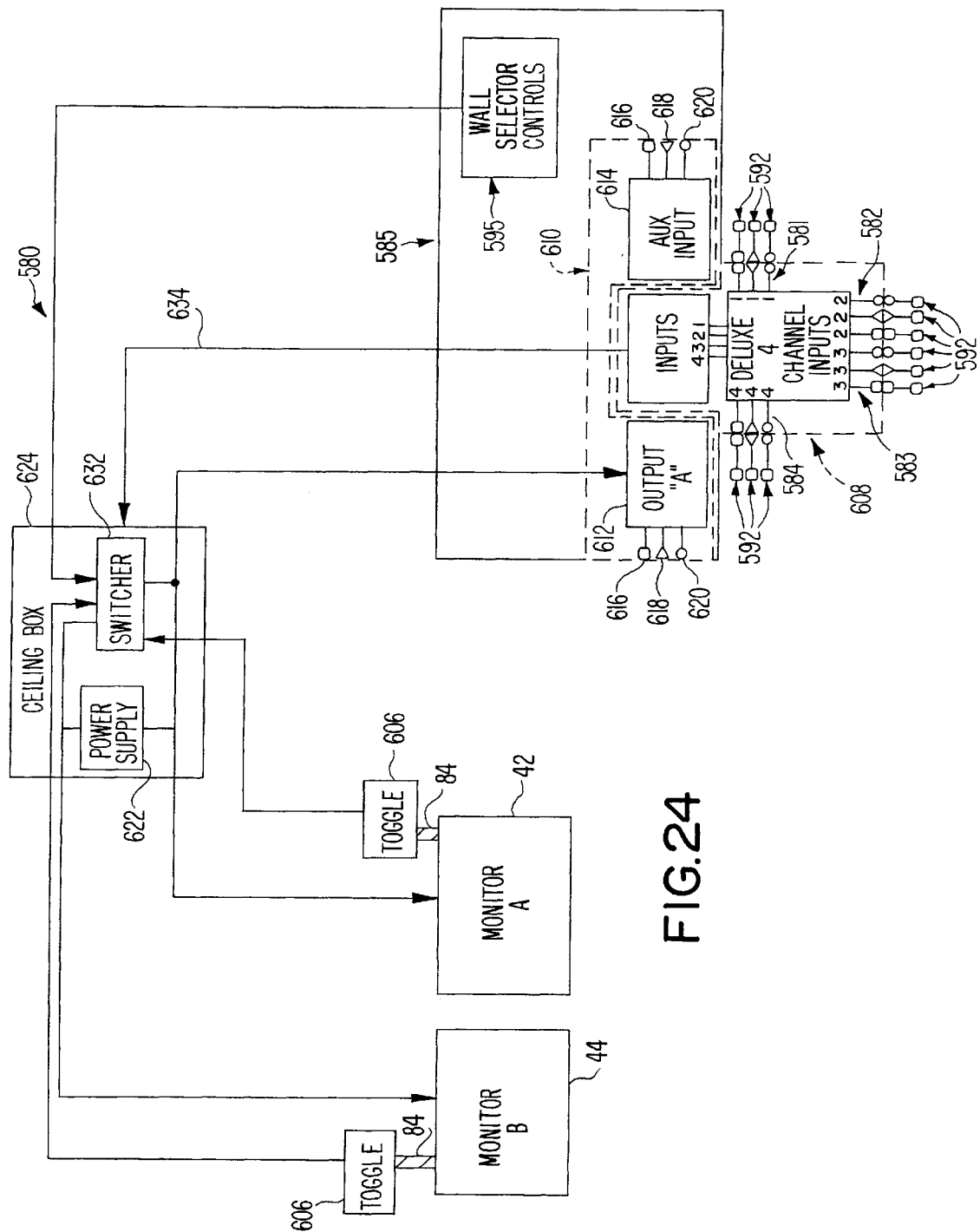
FIG. 24 is a diagrammatic view of the selector control panel and surgical theater system.

When a video device 592 is plugged into one of the channels 581–584, the connector of the video device 592 is coupled to the similarly configured connector 586, 588, 590 of the channel 581–584, as shown, for example, in FIG. 24. The appropriate connector 586, 588, 590 is selected as the active connector corresponding to the connector 586, 588, 590 to which the video device 592 is coupled by toggling of the selector switch 594. Indicator lights 596, 598, 600, such as LEDs, are provided adjacent to each connector 586, 588, 590 of each channel 581–584. When a specific connector 586, 588, 590 is selected as the active connector, the indicator light 596, 598, 600 corresponding to that connector 586, 588, 590 is lit.

Because there are four channels 581–584 each having three connectors 586, 588, 590, up to twelve video devices 592 can be coupled to the surgical theater system 10 although only one video device 592 per channel 581–584 will have its video feed available for display on a monitor 42 and 44 of the surgical theater system at any time. While the illustrated embodiment, shows three inputs (each input corresponding to a connector 586, 588, 590) per channel and four channels 581–584 in the system, it is within the scope of the disclosure as currently perceived to provide a selector system with fewer or more connectors or channels.

The illustrated selector control panel 585 may be located remotely from the surgical theater system 10. It is within the teaching of the disclosure for the selector control panel 585 to be mounted to a wall of the OR suite, to a separate boom in the OR suite, to some other location remote from the surgical theater system 10, or to the surgical theater system 10. For purposes of this description, the selector control panel 585 will be described as being mounted to a wall of the OR suite at a location remote from the surgical theater system 10. As previously described, remotely mounted controls for the surgical lights are often mounted to walls of surgical suites and it is within the teaching of this invention to mount the selector control panel 585 in the vicinity of the wall mounted light controls.

Monitor input selector panel 595 allows a user to choose one of the four channels 581–584 to be the active channel having its video feed displayed on a first or "A" monitor 42 of the surgical theater system 10 and to choose the same channel 581–584, or another of the four channels 581–584, as the active channel to have its video feed displayed on a second or "B" monitor 44 of the surgical theater system 10. In the illustrated embodiment, monitor input selector panel 595 includes an "A" monitor selector sub-panel 597 and a "B" monitor selector sub-panel 599. Each sub-panel 597 and 599 is provided with a selector button 604 and a channel selector LED array 602 including four LED's each of which is associated with one of the four channels 581–584.

In the illustrated embodiment, pushing the selector switch 604 causes the active channel for the monitor associated with the sub-panel 597 and 599 to toggle through the available channels. The appropriate LED in the channel selector LED array 602 is illuminated to indicate the active channel for the sub-panel 597 and 599. In the illustrated embodiment, channel 1 581 is the active channel for the "A" monitor 42 as indicated by the illumination of the LED associated with channel 1 of the LED array 602 of sub-panel 597 and channel 3 583 is the active channel for the "B" monitor 44 as indicated by the illumination of the LED associated with channel 3 of the LED array 602 of sub-panel 599. Thus, similar or different images can be selected for viewing on each of the monitors 42 and 44 of a two monitor surgical theater system 10.

In an embodiment of surgical theater system 10, a duplicate selector switch 606 is located in the sterile handle 84 of each monitor 42 and 44, as shown, for example, in FIGS. 24, 16 and 17. This duplicate selector switch 606 allows a surgeon or some other operating room personnel to select which image is visible on the monitor 42 and 44 to which the handle 84 is attached without moving away from the monitor 42 and 44. Pushing the duplicate switch 606 toggles through each available channel 581–584 to alter the active channel for the associated monitor 42 and 44 and induces the associated LED for the active channel of the LED array 602 to be illuminated on the associated sub-panel 597 and 599.

Figure 23:
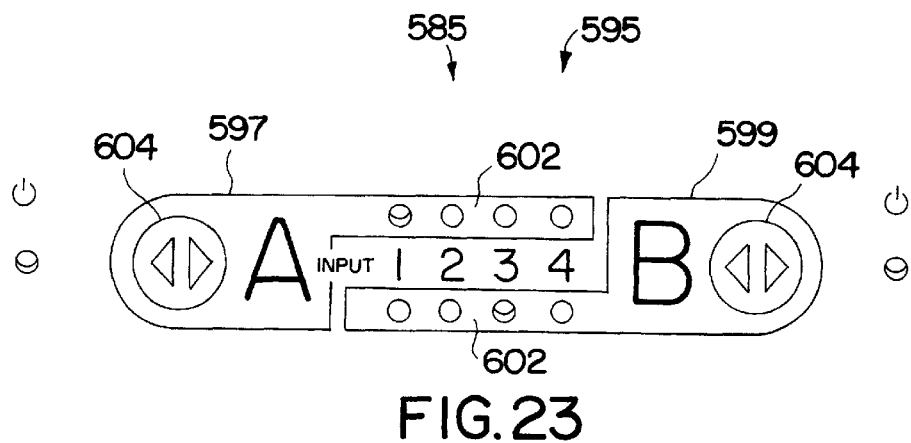
FIG. 23 is a plan view of a remotely mounted monitor input selector panel of the selector control panel for selecting the channel to be displayed on "A" and "B" monitors of the surgical theater system, an active channel selector button is provided for each monitor allowing an active channel to be selected so that the video feed present on that channel will be displayed on the appropriate monitor, indicator lights are associated with channels to indicate the active channel of each monitor.

As shown for example in FIGS. 23 and 24, selector control panel 585 also includes an output panel 610 allowing the images on any channel 581–584 to be provided to a remote monitor, VCR, printer, computer, or other device if desired. Included in the output panel 610 are an "A" monitor output sub-panel 612 and an input 1 auxiliary output sub-panel 614. Each sub-panel 612 and 614 includes a plurality of connectors, illustrated as a y-c connector 616, a composite connector 618, and an RGB connector 620.

The connectors 616, 618, 620 of the "A" monitor output sub-panel 612 are coupled to the video signal selected for the "A" monitor 42 allowing the same image to be displayed on a remote monitor as is being displayed on the "A" monitor 42 of the surgical theater system 10. The "A" monitor 42 will usually be selected by the surgeon as the main monitor so that the "A" monitor output is used for another peripheral or remote monitor or support device. In the illustrated embodiment, the "A" monitor output sub-panel 612 includes three indicator lights 626, 628, 630, such as LEDs, associated with connectors 616, 618, 620 respectively to indicate the type of signal which is being transmitted and therefore the active connector. If a slave monitor is coupled to the "A" monitor output sub-panel 612, the slave is preferably coupled to all three output connectors 616, 618, 620 to guarantee that an image will always appear on the slave monitor.

Referring to FIG. 24, the connectors 616, 618, 620 of input 1 auxiliary output sub-panel 614 are shown to be a direct feed from the primary input 1 present on channel 1 581. Any device that is plugged into connectors 586, 588, 590 of channel 1 581 will feed a signal directly to the connectors 616, 618, 620 respectively of auxiliary output sub-panel 614. The output of sub-panel 614 can be used as an emergency output since it is a direct signal from the input panel 608 and doesn't travel through the arm system to the monitor. If anything fails in the monitor 42 and 44 or arm system, a signal is still available from the auxiliary output sub-panel 614.

As shown in FIG. 24, power supply 622 to the surgical theater system, including the first monitor 42 and second monitor 44, and the selector panel 585 is mounted in a ceiling box 624. Power supply 622 is a low voltage medical grade power supply producing twelve volts. Illustratively, power supply 622 is made by International Power Sources, Inc., Holliston, Mass., 01746 as model # PM200-13C. A switcher 632 is also mounted in the ceiling box 624. Switcher 632 is electrically coupled to first monitor 42, second monitor 44, duplicate switches 606 on the handle 84 of each monitor 42 and 44, input panel 608, wall selector control panel 595, and "A" monitor output sub-panel 612. Power to switcher 632 is supplied by power supply 622. Video signals from the active input of each channel 581–584 are electrically coupled to switcher 632 through video bus 634. As previously mentioned, the channel 1 input is directly coupled to the auxiliary output sub-panel 614. Illustratively, inputs are available from four channels 581–584, each of which may be coupled to as many as three input devices 592. It is within the scope of the disclosure as presently perceived to configure each channel to receive as few as one video input or more than three video inputs.

In response to signals received from the wall selector control panel 595 and the toggle 606 on the handle 84 of each monitor 42 and 44, switcher 632 selects from the video signals received from inputs and routes video signals to the "A" monitor 42, "B" monitor 44, and output sub-panel 612. Output sub-panel 612 receives the same video feed as "A" monitor 42. "B" monitor 44 may receive the same or a different video feed as "A" monitor 42.

Figure 25:
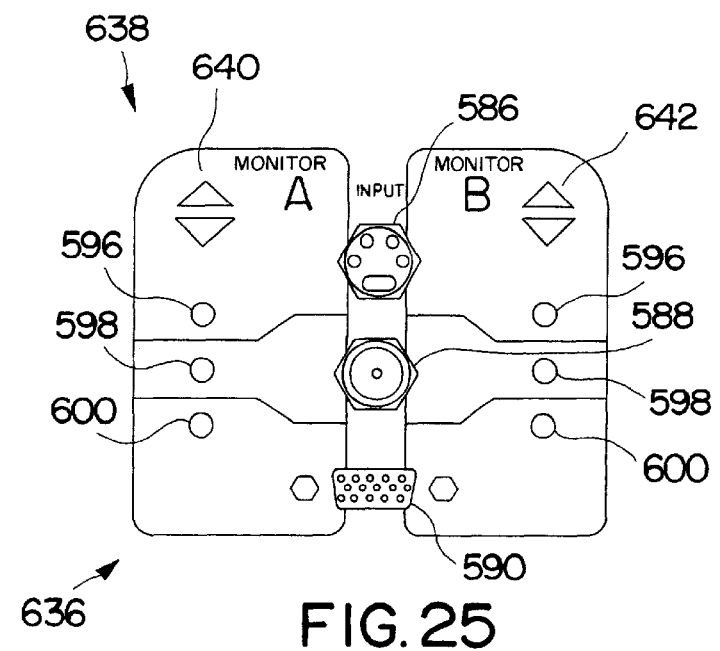
FIG. 25 is a plan view of a remotely mounted input controller of an alternative selector control panel electrically coupled to the monitors of the surgical theater system showing controls for dedicated input channels for each monitor both of which share three connectors to which video devices may be coupled to provide a video image to the monitors of the surgical theater system or another monitor coupled to a remote output, each input channel controller is provided with a selector switch by which an active connector is selected and indicator lights configured to display which of the three connectors is active.
Figure 26:
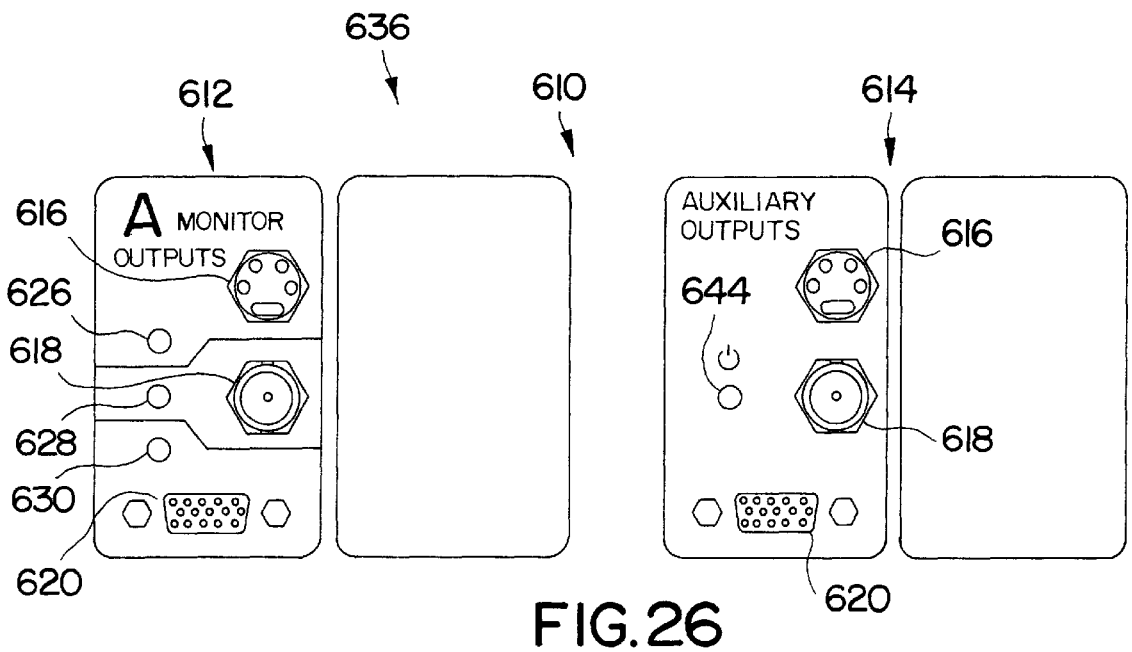
FIG. 26 is a plan view of a remotely mounted output panel of the alternative selector control panel showing an "A" monitor output sub-panel electrically coupled to the video feed of the primary or "A" monitor of the surgical theater system and an Auxiliary output sub-panel directly coupled to the inputs of the input controller each output sub-panel includes three connectors to permit monitors or other video display devices to be coupled thereto.

Portions of an alternative selector device 636 are shown in FIGS. 25 and 26. Selector device 636 includes an alternative dedicated input panel 638 and an output panel 610. Output panel 610 of selector device 636 is substantially identical to output panel 610 of selector device 580 described above except for the connection of output sub-panel 614. Nevertheless, identical reference numerals will be used in describing output panel 610 of selector device 636 as were used in describing output panel 610 of selector device 580.

Input panel 638 includes three differently configured connectors (a y-c connector 586, a composite connector 588, and an RGB connector 590), an "A" monitor selector button 640, a "B" monitor selector button 642 and two sets of three indicator lights 596, 598, 600 associated with connector 586, 588, 590. Actuation of "A" monitor selector button 640 selects one of the three connectors 586, 588, 590 as the active connector providing the video feed to "A" monitor 42 and "A" monitor output sub-panel 612. Actuation of "A" monitor selector button 640 also induces the appropriate one of the three "A" monitor indicator lights 596, 598, 600 to indicate which connector 586, 588, 590 respectively is the active connector for "A" monitor 42. Actuation of "B" monitor selector button 642 selects one of the three connectors 586, 588, 590 as the active connector providing the video feed to "B" monitor 44. Actuation of "B" monitor selector button 642 also induces the appropriate one of the three "B" monitor indicator lights 596, 598, 600 to indicate which connector 586, 588, 590 respectively is the active connector for "B" monitor 44.

Output panel 610 of selector device 636 includes "A" monitor output sub-panel 612 and Auxiliary output sub-panel 614. "A" monitor output sub-panel 612 is identical to "A" monitor output sub-panel 612 of selection device 580 and receives the video feed being sent to "A" monitor 42. Auxiliary output sub-panel 614 of selector device 636 is similar to channel 1 auxiliary output sub-panel 614 of selector device 580 in that it is directly coupled to the input panel 638, however, auxiliary output sub-panel 614 may receive any video feed which is live. Auxiliary output panel sub-panel 614 includes an indicator light 644, such as an LED to indicate that the system is powered on.

Both selector device 580 and selector device 636 are intended for use with a surgical theater system 10 including a first and second monitor 42 and 44. Those skilled in the art will recognize that selector device 636 can be mounted in similar locations as selector device 580 and can be coupled to a surgical theater system 10 in a similar manner as is shown in FIG. 24. Selector device 636 has fewer channels than selector device 580. Because selector device 636 includes only one of each type of connector 586, 588, 590, the number and type of video devices 592 which may be coupled to a surgical theater system 10 is more limited with selector device 636 than with selector device 580. In the illustrated configuration, without an external splitter, only three remote video devices 592, each having a different type of connector may be coupled to the monitors 42 and 44 of a surgical theater system 10 when selector device 636 is used.

Cameras are used in operating rooms as a means of networking with the rest of the world. The camera has now become the vehicle by which surgeons can consult with each other during live procedures. For certain surgical procedures it is not uncommon for surgeons to consult with each other from different parts of the world during a case (commonly referred to as 'Telesurgery'). Thus although not specifically illustrated, many cameras used in surgical suites include or are coupled to microphones and speakers permitting audio as well as video signals to be recorded and transmitted. In teaching hospitals, clinical educators require interactive filming capabilities that can be controlled remotely from the classroom. Such procedures are either recorded for critique at a later date or simply observed 'real time' for teaching. Surgeons routinely record procedures and edit the content for presentation at a conference. More surgical procedures are being recorded for future reference should the outcome of the surgery be questioned.

Figure 27:
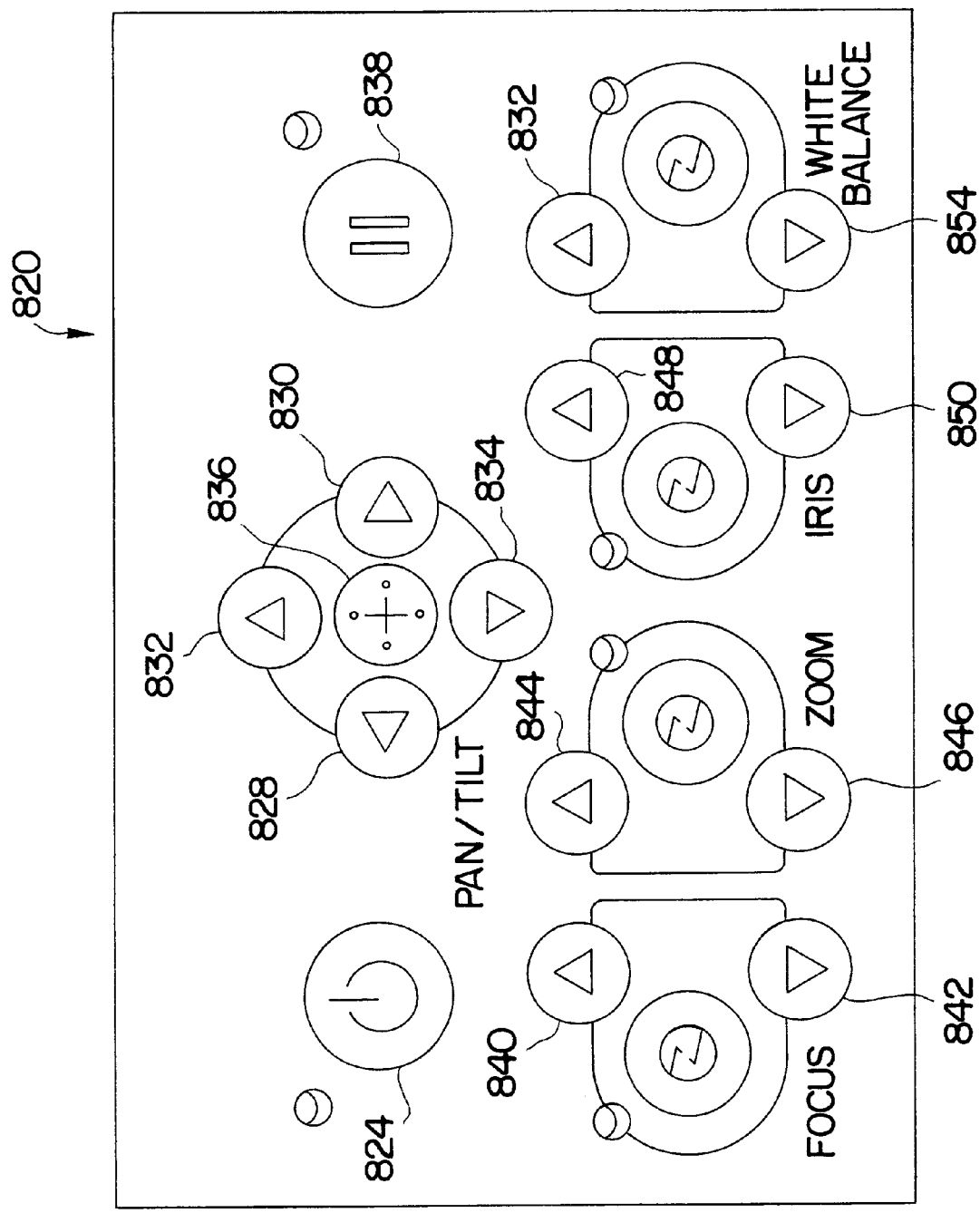
FIG. 27 is a plan view of a remotely mounted camera control panel for controlling the camera of a surgical theater system, the control panel includes buttons coupled to the camera and camera mount for controlling the pan/tilt, focus, zoom, iris, white balance, pause, and on/off functions of the camera and camera mount.
Figure 28:
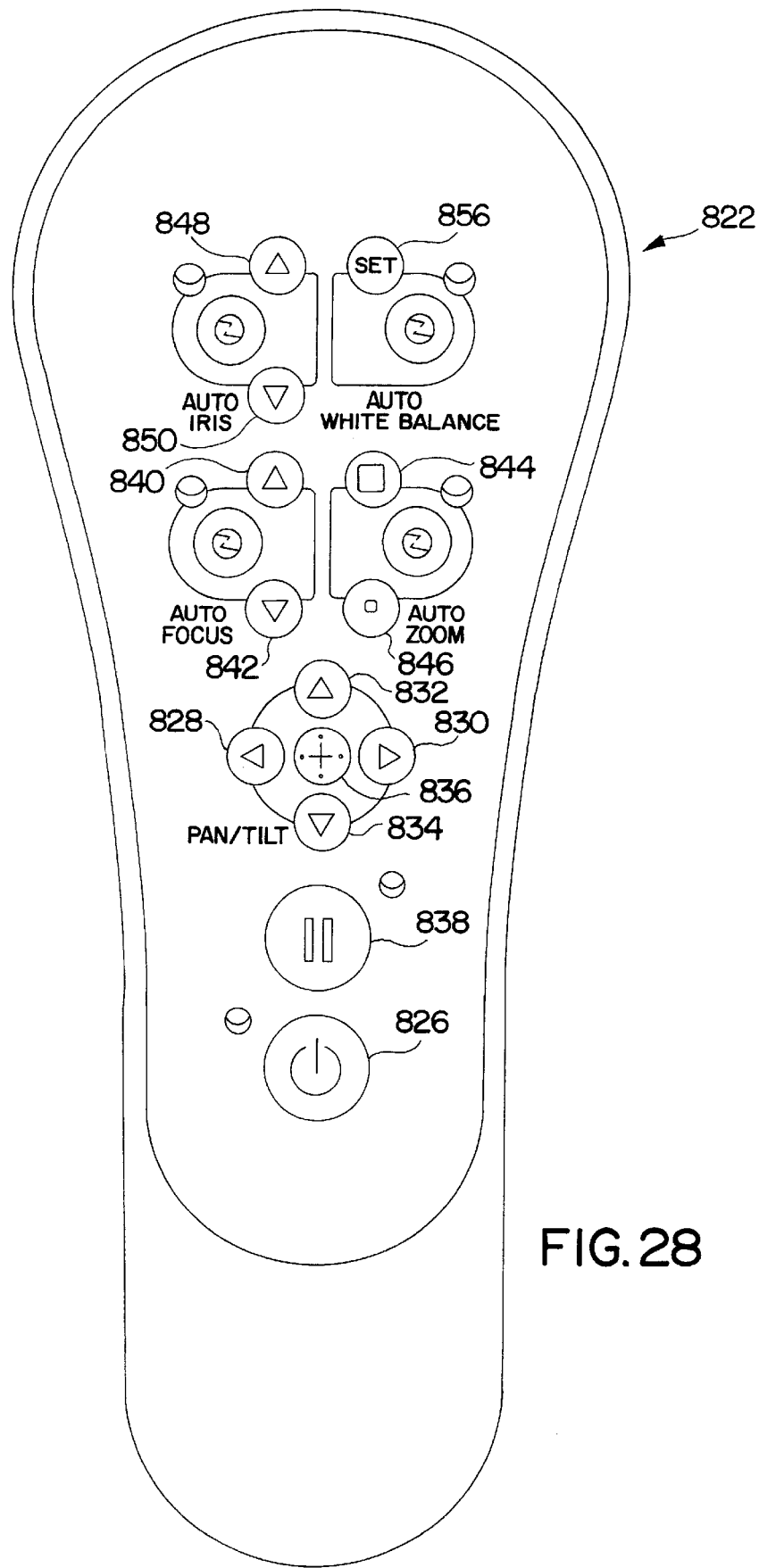
FIG. 28 is a plan view of a wireless camera remote control for wirelessly controlling the same camera functions as the camera control panel of FIG. 27.

As was explained above, camera 108, camera arm 790 and camera mount 647 may include mechanisms and drives facilitating remote control of panning, zooming, tilting, white balancing, and iris adjustment. To facilitate remote operation of such a camera 108 and camera mount 647 attached to a multi-purpose arm 648, camera arm 790 attached to a multi-purpose receptacle 745, or any other properly wired arm attached to a surgical light apparatus, a camera wall control panel 820 as well as a wireless remote control 822 is provided, as shown, for example, in FIGS. 27 and 28. It is also envisioned, although not illustrated, that a wired remote control be provided to facilitate control of the camera 108 from a remote conference room. It will be understood that such a wired remote control will include a control panel having buttons similar to those illustrated in FIG. 27. Camera 108 and its mounting mechanism may be manually positioned enabling the doctor to point the camera at the surgical sight. A pan/tilt mechanism 711 and 811 allows the camera to be remotely tilted up or down and panned left or right by after initial set up. To simplify the mounting mechanism and to take advantage of commonly available camera pan and tilt drives, it is envisioned that the degree of freedom of pan and tilt remotely controlled motion may be limited such as by plus or minus forty-five degree of the manually adjusted home position.

Each control panel 820 and remote control 822 is provided with an on/off button 824 and 826, two pan buttons 828 and 830, two tilt buttons 832 and 834, a home position button 836, a pause button 838, two focus buttons 840 and 842, two zoom buttons 844 and 846, two iris buttons 848 and 850, and either two white balance buttons 852 and 854 or a white balance set button 856. As previously mentioned the surgeon or other OR personnel may manually adjust camera mount 647 or camera arm 790 to point camera 108 at an initial position, such as the surgical sight. If prior to manual adjustment, the mechanisms controlling the pan and tilt are adjusted to a central position half way between their limits of travel, such position being referred to herein as the home position, then actuation of the home button 830 causes the camera to return to pointing at the surgical sight (or any other initial position).

Each On/Off button 824 and 826 is coupled to a switch that controls the supply of power to the camera 108. Each pan button 828 and 830 is coupled to a motor control circuit for controlling the motor which actuates panning of the camera 108. When the pan left button 828 is actuated, the pan motor is controlled to induce the camera mount to rotate the field of view of the camera 108 to the left. When the pan right button 830 is actuated, the pan motor is controlled to induce the camera mount to rotate the field of view of the camera 108 to the right. Actuation of the tilt up button 832 controls the tilt motor to induce the field of view of the camera 108 to rotate upwardly. Actuation of the tilt down button 834 controls the tilt motor to induce the field of view of the camera 108 to rotate downwardly.

The two focus buttons 840 and 842 are coupled to internal motors of the camera 108 that control the position of the lens in order to adjust the focus of the camera 108. Pushing the first focus button 840 induces the camera motor to move the lens in a first direction to adjust the focus and pushing the second focus button 842 induces the camera motor to move the lens in the opposite direction to adjust the focus.

Similarly, the two zoom buttons 844 and 846 are coupled to internal motors and mechanisms of the camera 108 which adjust the relative position of the compound lenses to increase or decrease the magnification of the compound lenses. Pushing the zoom in button 844 induces the camera motor to move the position of the compound lenses in a first direction to increase the effective magnification of the compound lenses and pushing the zoom out button 846 induces the camera motor to move the position of the compound lenses in the opposite direction to decrease the effective magnification of the compound lenses.

The iris buttons 848 and 850 are coupled to internal motors and mechanisms of the camera 108 which adjust the aperture diameter of the iris of the camera 108. Pushing the aperture open button 848 induces the internal motors to increase the aperture diameter of the camera 108 while pushing the iris closed button 850 induces the internal motors to decrease the aperture diameter of the iris.

The white balance buttons 852 and 854 and white balance set button 856 are coupled to internal mechanisms of the camera 108 that increase and decrease the white balance of the video image produced by the camera 108. Actuation of the white balance increase button 852 increases the white balance of the video image while actuation of the white balance decrease button 854 decreases the white balance of the video image. Actuation of the white balance set button 856 induces internal controls to automatically set the white balance to a desired setting.

Each of the buttons with evenly numbered reference numerals between 824–856 are referred to above as being coupled to a motor or mechanism of the camera 108 or camera mount. This coupling occurs through hard wire connections in the case of camera wall control panel 820 or a hard wired suite remote (not shown). In the case of a wireless remote control 822, the remote includes a transmitter that transmits appropriate signals to a receiver that is hardwired to the camera 108 and camera mount. It is envisioned that transmission may be by RF, UV, IR, optical or other types of signals commonly used to remotely transmit signals and data. Preferably such signals will be conducive to use in a health care environment to avoid interference with other healthcare equipment.

When a camera 108 is mounted by a camera mount 647 to a multipurpose arm 648, by a camera arm 790 to a multi-purpose receptacle 745, or by a camera mounting arm assembly 90, integration of the camera 108 with the selector controls 580, 636 may occur in several ways. One method is to hard wire the wires carrying the video signal from the camera 108 into the monitor control panel 585 and 636 primary input of the RGB signal (coupled to connector 590). When hard wired, a blank RGB plug labeled "Camera" is permanently fastened into the RGB input connector 590 to the monitor control panel 585 and 636 to indicate that this input is always the camera 108. A second alternative is to couple the video output of the camera 108 to an output plate (not shown), mount the camera output plate including a video connector adjacent to the monitor control panel 585 and 636 and provide a pigtail connector to couple the video output of the camera 108 to the monitor control panel 585 and 636. When it is envisioned that cameras and monitors may be moved between surgical light assemblies located in different OR suites, it is preferable that the camera video output be integrated by the same method in all of the suites for system integrity.

Figure 29:
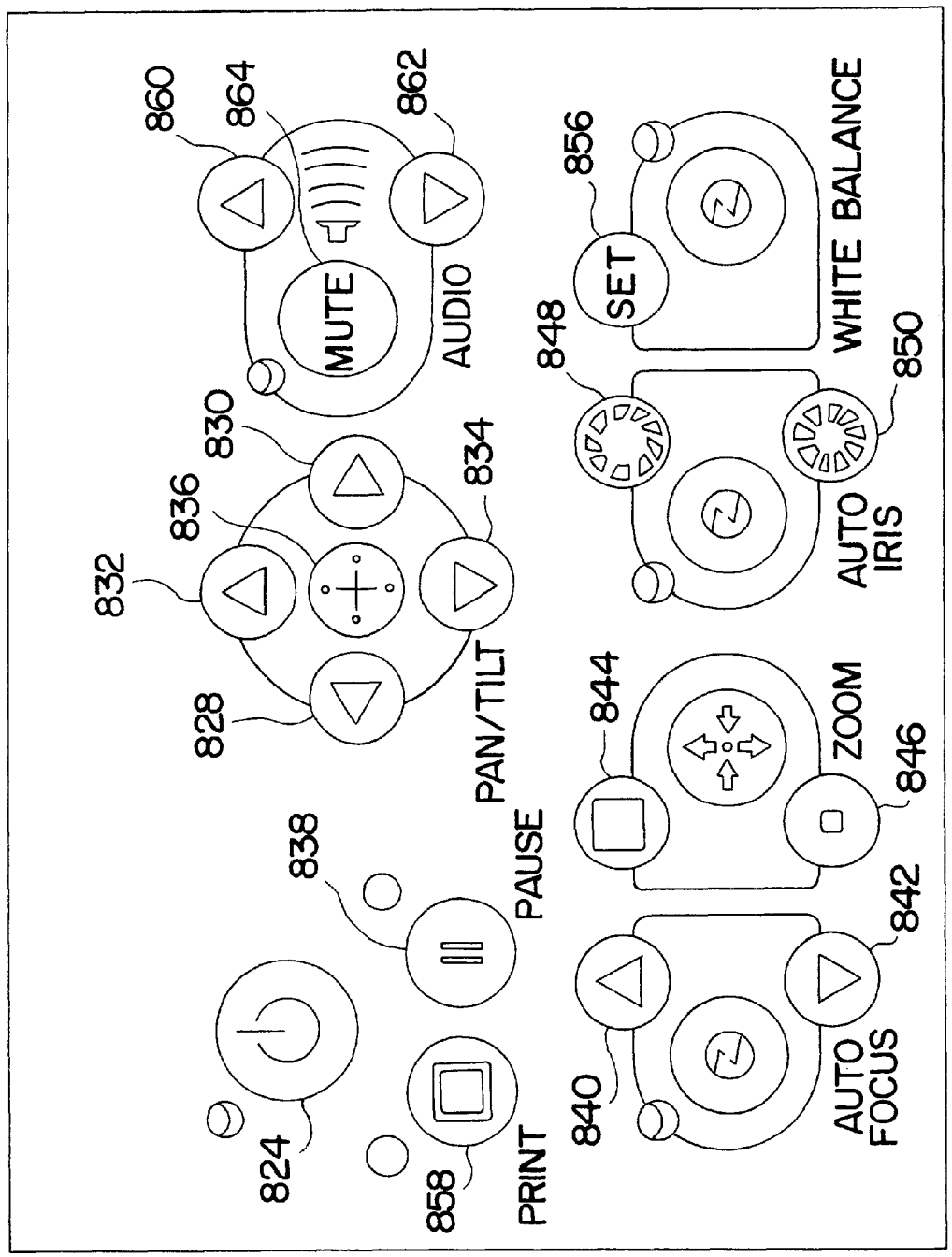
FIG. 29 is a plan view of a remote control panel similar to the panel of FIG. 27 for coupling to a camera of a surgical theater system including a sound system, the control panel includes buttons coupled to the camera and camera mount for controlling the pan/tilt, focus, zoom, iris, white balance, pause, print audio, and on/off functions of the camera and camera mount.

Referring to FIG. 29 there is shown an alternative camera control panel 920. Camera control panel is similar to control panel 820 shown in FIG. 22 except panel 920 includes additional buttons not included in panel 820 to facilitate freezing and image and printing the frozen image and facilitating volume adjustment and muting of audio functions. Buttons of control panel 920 which function identically as buttons of control panels 820 and 822 will be identified with the same reference numerals and will not be further described hereafter, it being understood that the description above of those buttons with regard to control panels 820 and 822 are likewise applicable to control panel 920.

In addition to the buttons described above with regard to remote controls 820 and 822, control panel 920 includes print button 858, volume increase button 860, volume decrease button 862, and mute button 864. The output panels each include at least one RGB connector 620 to facilitate attaching a printer or a computer including a printer to the surgical theater system 10. Pressing pause button 838 causes the video image from the camera to be frozen. Subsequently pressing the print button causes a signal to be sent to the printer to cause the frozen image to be printed. When the volume increase button 860 is actuated, a volume controller (not shown) to a speaker (not shown) is actuated to increase the volume of the output of the speaker. When the volume decrease button 860 is actuated, a volume controller (not shown) to a speaker (not shown) is actuated to decrease the volume of the output of the speaker. When the mute button 864 is actuated, the output of the speaker is muted.

Although the invention has been described in detail with reference to a certain preferred embodiment, variations and modifications exist within the scope and spirit of the present invention as described and defined in the following claims.

What is claimed is:

1. A surgical light apparatus comprising a hub assembly configured to be attached to a ceiling, an arm coupled for pivotal movement about the hub assembly, a monitor attached to the arm, a video input controller electrically coupled to the monitor, the video input controller including a first channel input having a video coupling for attachment to a first video input device providing a first video feed, a second channel input having a video coupling for attachment to second video device providing a second video feed, and a channel controller coupled to the monitor, first channel input, and second channel input, the channel controller being configured to select a video feed to the monitor.

2. The surgical light apparatus of claim 1 wherein the first channel input includes a plurality of video couplings.

3. The surgical light apparatus of claim 2 further comprising a first selector to select between the plurality of video couplings as a source of a first video feed.

4. The surgical light apparatus of claim 2 wherein the second channel input includes a plurality of video couplings.

5. The surgical light apparatus of claim 4 further comprising a second selector to select between the plurality of video couplings as a source of a second video feed.

6. The surgical light apparatus of claim 1 further comprising a third channel input having a video coupling for attachment to a third video device providing a third video feed.

7. The surgical light apparatus of claim 6 further comprising a fourth channel input having a video coupling for attachment to a fourth video device providing a fourth video feed.

8. The surgical light apparatus of claim 1 further comprising a second arm coupled for pivotal movement about the hub assembly, a second monitor attached to the second arm and electrically coupled to the channel controller of the video input controller, and wherein the channel controller is configured to select a video feed to the second monitor.

9. The surgical light apparatus of claim 8 further comprising an output panel including a connector configured for connection to a remote video display device, the connector being coupled to the video feed selected for the first monitor.

10. The surgical light apparatus of claim 9 wherein the output panel further comprises a second connector configured for connection to a remote video display device, the second connector being directly coupled to one of the first, second, third, and fourth video feeds.

11. The surgical light apparatus of claim 1 further comprising a camera coupled by a camera arm for pivotal movement about the hub.

12. The surgical light apparatus of claim 11 wherein the camera is mounted to the camera arm to facilitate remote manipulation of the field of view of the camera and further comprising a camera controller electrically coupled to the camera arm, the camera controller being located at a remote location from the remainder of the surgical light apparatus.

13. A surgical light apparatus comprising a hub assembly configured to be attached to a ceiling, an arm coupled for pivotal movement about the hub assembly, a monitor mounted on a monitor mount attached to the arm, the monitor mount including a handle on which an actuator button is mounted, a video input controller electrically coupled to the monitor, the video input controller including a first channel input having a video coupling for attachment to a first video input device providing a first video feed, a second channel input having a video coupling for attachment to second video device providing a second video feed, and a channel controller coupled to the monitor, first channel input, and second channel input, the channel controller being coupled to the actuator button and being configured to select a video feed to the monitor in response to actuation of the actuator button.

14. The apparatus of claim 13 wherein the handle is sterilizable.

15. The apparatus of claim 13 wherein the actuator button includes a channel increase and decrease button.

16. A surgical light apparatus comprising a hub assembly configured to be attached to a ceiling, an arm coupled for pivotal movement about the hub assembly, a camera mount mounted to the arm, the camera mount including a handle on which an actuator is mounted, a camera mounted on the camera mount, the camera including an on/off function, automated zoom capabilities, and automated focus capabilities, and wherein actuation of the actuator controls the on/off function of the camera.

17. The apparatus of claim 16 wherein the handle is sterilizable.

18. The apparatus of claim 16 and comprising a second actuator mounted on the handle and wherein actuation of the second actuator controls the zoom capabilities of the camera.

19. The apparatus of claim 18 and comprising a third actuator mounted on the handle and wherein actuation of the third actuator controls the focus capabilities of the camera.

20. The apparatus of claim 19 wherein the handle includes a longitudinal axis, the handle is mounted to the remainder of the camera mount for pivotal movement of the handle about the longitudinal axis, and pivotal movement of the handle actuates the second actuator.

21. The apparatus of claim 16 and comprising a third actuator mounted on the handle and wherein actuation of the third actuator controls the focus capabilities of the camera.

* * * * *